United States Patent
Cañeque et al.

(10) Patent No.: US 12,415,781 B2
(45) Date of Patent: Sep. 16, 2025

(54) COMPOUNDS WITH BIGUANIDYL RADICAL AND USES THEREOF

(71) Applicants: INSTITUT CURIE, Paris (FR); CENTRE NATIONAL DE LA RECHERCHE SCIENTIFIQUE, Paris (FR); INSERM (INSTITUT DE LA SANTÉ ET DE LA RECHERCHE MÉDICALE), Paris (FR)

(72) Inventors: Tatiana Cañeque, Paris (FR); Sebastian Muller, Ivry-sur-Seine (FR); Raphaël Rodriguez, Vers-Pont-du-Gard (FR)

(73) Assignees: INSTITUT CURIE, Paris (FR); INSERM (INSTITUT NATIONAL DE LA SANTÉ ET DE LA RECHERCHE MÉDICALE), Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 1209 days.

(21) Appl. No.: 15/734,569

(22) PCT Filed: Jun. 4, 2019

(86) PCT No.: PCT/EP2019/064422
§ 371 (c)(1),
(2) Date: Dec. 3, 2020

(87) PCT Pub. No.: WO2019/233982
PCT Pub. Date: Dec. 12, 2019

(65) Prior Publication Data
US 2021/0230105 A1 Jul. 29, 2021

(30) Foreign Application Priority Data
Jun. 5, 2018 (EP) .................................... 18305683

(51) Int. Cl.
*A61K 45/06* (2006.01)
*A61P 35/00* (2006.01)
*C07C 279/26* (2006.01)
*C07D 405/12* (2006.01)

(52) U.S. Cl.
CPC .......... *C07C 279/265* (2013.01); *A61K 45/06* (2013.01)

(58) Field of Classification Search
CPC ... C07C 279/265; A61P 35/00; C07D 405/12; A61K 45/06; C07F 9/5442
See application file for complete search history.

(56) References Cited

U.S. PATENT DOCUMENTS

2015/0342909 A1 12/2015 Potter et al.
2023/0416196 A1* 12/2023 Rodriguez .......... C07C 279/265

FOREIGN PATENT DOCUMENTS

| CN | 105 367 572 | 3/2017 |
| EP | 2 522 653 | 11/2012 |
| EP | 3 222 614 | 9/2017 |
| WO | WO 2007/112121 | 10/2007 |
| WO | WO 2011/147528 | 12/2011 |
| WO | WO 2016/025725 | 2/2016 |

OTHER PUBLICATIONS

Muller et al., PLOS One, 2018, 13(11).*
Ishida, T. et al. "Synthesis of Alkylendibiguanides from Alkylendiamines by the Guanyl-O-alkylisourea Method" *Journal of Synthetic Organic Chemistry*, 1970, pp. 1045-1049, vol. 28, No. 10, abstract only.
Written Opinion in International Application No. PCT/EP2019/064422, Sep. 11, 2019, pp. 1-10.

* cited by examiner

*Primary Examiner* — Sun Jae Yoo
(74) *Attorney, Agent, or Firm* — SALIWANCHIK, LLOYD & EISENSCHENK

(57) ABSTRACT

The present invention relates to new compounds of formula (I), and their uses.

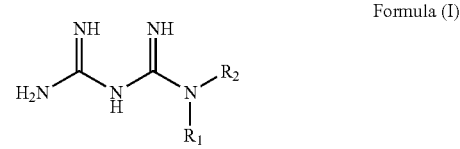

Formula (I)

24 Claims, 6 Drawing Sheets

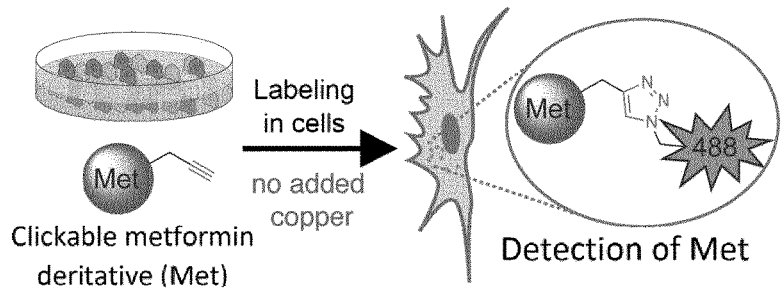
FIGURE 3B
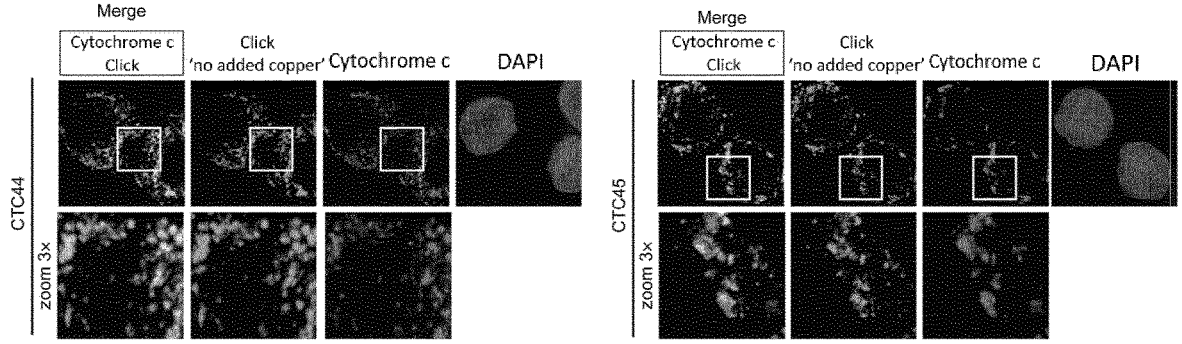
FIGURE 4A
FIGURE 4B
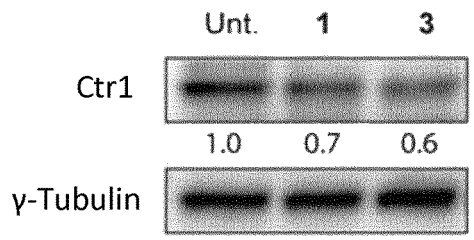
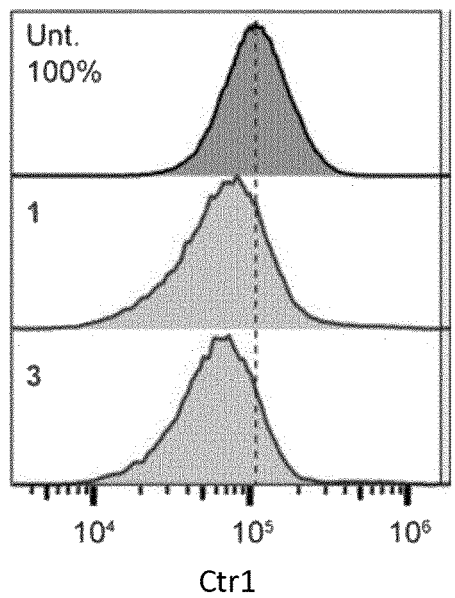

COMPOUNDS WITH BIGUANIDYL RADICAL AND USES THEREOF

CROSS-REFERENCE TO RELATED APPLICATION

This application is the U.S. national stage application of International Patent Application No. PCT/EP2019/064422, filed Jun. 4, 2019.

FUNDING

The project leading to this application has received funding from the European Research Council (ERC) under the European Union's Horizon 2020 research and innovation program (grant agreement No [647973]).

FIELD OF THE INVENTION

The present invention relates to the field of medicine, and in particular of oncology. It relates to new compounds comprising biguanidyl radical.

BACKGROUND OF THE INVENTION

A variety of derivatives of biguanide are used as pharmaceutical drugs. Most of them are used as antihyperglycemic agents, in particular for used for the treatment of diabetes mellitus and prediabetes. The most widely used drug is metformin.

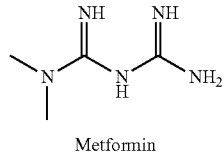

Metformin

Derivatives of biguanide are also used as antimalarial drugs such as proguanil and chlorproguanil and as disinfectants such as chlorhexidine, polyaminopropyl-biguanide, polyhexanide, and alexidine.

More recently, metformin and derivatives thereof have been described for their use in the treatment of cancer (Safe et al, 2018, Biol Chem, 399, 321-335; WO2017/192602). More particularly, patent applications disclose derivatives of metformin (EP2522653, EP3222614, WO2013/022279, WO2014/123364, WO2015/160220, WO2016/025725 and WO2016/155679).

However, there is a constant need of new drugs, especially for the treatment of cancers.

SUMMARY OF THE PRESENT INVENTION

The inventors provide new compounds comprising biguanidyl radical which are more potent than metformin for the treatment of cancer. In addition, they identified that the compounds of the present invention target the mitochondrial copper and are able to selectively target the population of cancer cells with mesenchymal features.

Accordingly, the present invention relates to a compound of formula (I)

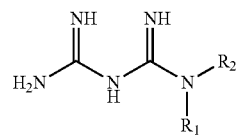

Formula (I)

wherein $R_1$ is selected from the group consisting of a $C_1$-$C_6$ alkyl, —$(CH_2)_a$—C≡CH, —$(CH_2)_b$—$P^+Ph_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6, preferably 2 to 4, and "b" being an integer selected from 5 to 11, preferably 6 to 10, said alkyl, cycloalkyl, cycloheteroalkyl, aryl or heteroaryl being optionally substituted by a R group or a R' group; and $R_2$ is selected from the group consisting of
—$(CH_2)_d$—C≡CH, with "d" being an integer selected from 1 to 6; and
—$(CH_2)_e$—CH=$CH_2$ with "e" being an integer selected from 2 to 6;

or $R_1$ is selected from the group consisting of H, a $C_1$-$C_6$ alkyl, —$(CH_2)_a$—C≡CH, —$(CH_2)_b$—$P^+Ph_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6, preferably 2 to 4, and "b" being an integer selected from 5 to 11, preferably 6 to 10, said alkyl, cycloalkyl, cycloheteroalkyl, aryl or heteroaryl being optionally substituted by a R group or a R' group;

$R_2$ is selected from the group consisting of
—$(CH_2)_f$—$CR_4$=CH—CH=$CR_5$—$(CH_2)_g$—$R_3$ with $R_4$ and $R_5$ being H, a R group or forming together a six-member ring, optionally substituted by one or two R' groups or fused with a cycloalkyl, an aryl, a cycloheteroalkyl or a heteroaryl having 3 to 6 members, "f" and "g" being an integer independently selected from 1 to 3;

—$(CH_2)_f$—C≡C—C≡C—$(CH_2)_g$—$R_3$, with "f" and "g" being an integer independently selected from 1 to 3;

—$(CH_2)_i$—$R_3$, with "i" being an integer selected from 7 to 9, preferably 8;

—$(CH_2)_j$—CH[$(CH_2)_k$—$P^+Ph_3$]—$(CH_2)_l$—$R_3$ with "j" and "l" being integer independently selected from 1 to 6, and "k" being an integer selected from 1 to 6;

—$(CH_2)_m$-cyclobutanyl-$(CH_2)_n$—$R_3$ with "m" and "n" being an integer independently selected from 1 to 3; and —$(CH_2)_p$—$CHR_6$—CH=CH—$CHR_7$—$(CH_2)_q$—$R_3$ with $R_6$ and $R_7$ being H, a R group or forming together a 4-6 member ring, optionally substituted by one or two R' groups or fused with a cycloalkyl, an aryl, a cycloheteroalkyl or a heteroaryl having 3 to 6 members, "p" and "q" being an integer independently selected from 1 to 3; and $R_3$ is

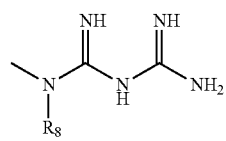

with $R_8$ selected from the group consisting of H, a $C_1$-$C_6$ alkyl, —$(CH_2)_a$—C≡CH, —$(CH_2)_b$—P$^+$Ph$_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6, preferably 2 to 4, and "b" being an integer selected from 5 to 11, preferably 6 to 10, said alkyl, cycloalkyl, cycloheteroalkyl, aryl or heteroaryl being optionally substituted by a R group or a R' group; and wherein R is selected from the group consisting of a $C_1$-$C_6$ alkyl, a $C_1$-$C_6$ alkyloxy, a $C_1$-$C_6$ halogenoalkyl, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, the group being optionally substituted by a group R', R' is selected from the group consisting of a $C_1$-$C_6$ alkyl, a $C_1$-$C_6$ alkyloxy, a $C_1$-$C_6$ thioalkyl, a halogen, a $C_1$-$C_6$ halogenoalkyl, a hydroxyl (—OH), a cyano (—CN), a nitro, an amino (—NH$_2$), a carboxyl (—COOH), a phosphate (PO$_4$), an amide (—CONH$_2$), —COOR", —NHR", —NR"R'", —COR", —CONHR", —NH-COR", —NHSO$_2$R", —SOR", —SO$_2$R", —SONR"R'", —SO$_2$NR"R'", a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, said cycloalkyl, cycloheteroalkyl, aryl or heteroaryl being optionally substituted by a halogen, a hydroxyl, a cyano, a nitro, an amino, or a $C_1$-$C_3$ alkoxy, with R" and R'" being H or a $C_1$-$C_6$ alkyl;

or a pharmaceutically acceptable salt thereof.

Preferably, $R_3$ is present in the compound.

Optionally, $R_2$ is selected from the group consisting of
—$(CH_2)_d$—C≡CH, with "d" being an integer selected from 2 to 4;
—$(CH_2)_e$—CH=CH$_2$ with "e" being an integer selected from 2 to 4;
—$(CH_2)_f$—CR$_4$=CH—CH=CR$_5$—$(CH_2)_g$—R$_3$ with $R_4$ and $R_5$ being H, a R group or forming together a six-member ring, optionally substituted by one or two R' groups or fused with a cycloalkyl, an aryl, a cycloheteroalkyl or a heteroaryl having 3 to 6 members, "f" and "g" being an integer independently selected from 1 to 3, and "f"+"g" being from 2 to 4;
—$(CH_2)_f$—C≡C—C≡C—$(CH_2)_g$—R$_3$, with "f" and "g" being an integer independently selected from 1 to 3, and "f"+"g" being from 2 to 4;
—$(CH_2)_i$—R$_3$, with "i" being an integer selected from 7 to 9;
—$(CH_2)_j$—CH[$(CH_2)_k$—P+Ph$_3$]—$(CH_2)_l$—R$_3$ with "j" and "l" being integer independently selected from 1 to 6, and "j"+"l" being from 5 to 7 and "k" being an integer selected from 2 to 4;
—$(CH_2)_m$-cyclobutanyl-$(CH_2)_n$—R$_3$ with "m" and "n" being an integer independently selected from 1 to 3, and "m+n" being from 2 to 4; and
—$(CH_2)_p$—CHR$_6$—CH=CH—CHR$_7$—$(CH_2)_q$—R$_3$ with $R_6$ and $R_7$ being H, a R group or forming together a 4-6 member ring, optionally substituted by one or two R' groups or fused with a cycloalkyl, an aryl, a cycloheteroalkyl or a heteroaryl having 3 to 6 members, "p" and "q" being an integer independently selected from 1 to 3, and "p"+"q" being from 2 to 4.

Optionally, $R_1$ is selected from the group consisting of a methyl, —$(CH_2)_a$—C≡CH and —$(CH_2)_b$—P$^+$Ph$_3$, with "a" being an integer selected from 2 to 4, and "b" being an integer selected from 6 to 10;

$R_2$ is selected from the group consisting of
—$(CH_2)_d$—C≡CH, with "d" being an integer selected from 2 to 4; and
—$(CH_2)_e$—CH=CH$_2$ with "e" being an integer selected from 2 to 6.

Optionally, $R_1$ is selected from the group consisting of H, a methyl, —$(CH_2)_a$—C≡CH and —$(CH_2)_b$—P$^+$Ph$_3$, with "a" being an integer selected from 2 to 4, and "b" being an integer selected from 6 to 10;

$R_2$ is selected from the group consisting of
—$(CH_2)_f$—CR$_4$=CH—CH=CR$_5$—$(CH_2)_g$—R$_3$ with $R_4$ and $R_5$ being H, "f" and "g" being an integer independently selected from 1 to 3, and "f"+"g" being from 2 to 4;
—$(CH_2)_f$—C≡C—C≡C—$(CH_2)_g$—R$_3$, with "f" and "g" being an integer independently selected from 1 to 3 and "f"+"g" being from 2 to 4;
—$(CH_2)_i$—R$_3$, with "i" being an integer selected from 7 to 9;
—$(CH_2)_j$—CH[$(CH_2)_k$—P+Ph$_3$]—$(CH_2)_l$—R$_3$ with "j" and "l" being integer independently selected from 1 to 6, "j"+"l" being from 5 to 7, and "k" being an integer selected from 1 to 6;
—$(CH_2)_m$-cyclobutanyl-$(CH_2)_n$—R$_3$ with "m" and "n" being an integer independently selected from 1 to 3 and "m+n" being from 2 to 4; and
—$(CH_2)_p$—CHR$_6$—CH=CH—CHR$_7$—$(CH_2)_q$—R$_3$ with $R_6$ and $R_7$ being H or forming together a 4-member ring, "p" and "q" being an integer independently selected from 1 to 3 and "p"+"q" being from 2 to 4; and $R_3$ is

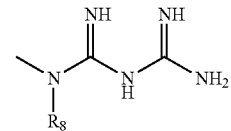

with $R_8$ selected from the group consisting of H, a methyl, $(CH_2)_a$—C≡CH and —$(CH_2)_b$—P$^+$Ph$_3$, with "a" being an integer selected from 1 to 6, preferably 2 to 4, and "b" being an integer selected from 5 to 11, preferably 6 to 10.

Optionally, at least one among $R_1$, $R_2$ and $R_8$ is —$(CH_2)_a$—C≡CH with "a" being an integer from 1 to 6.

Optionally, the compound is selected from the group consisting of

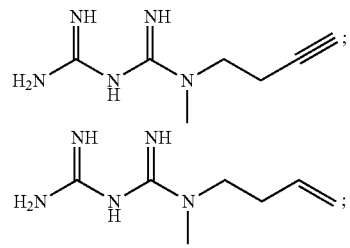

5
-continued
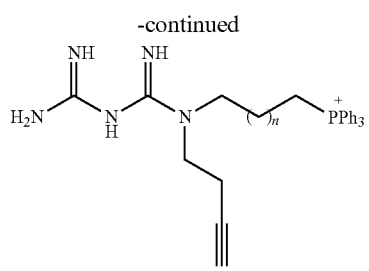
with n being an integer selected from 3 to 9;
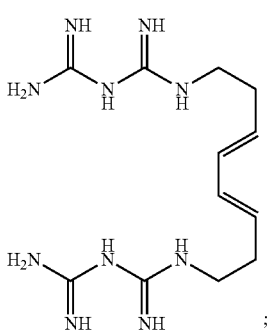
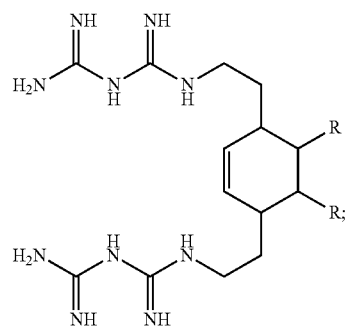
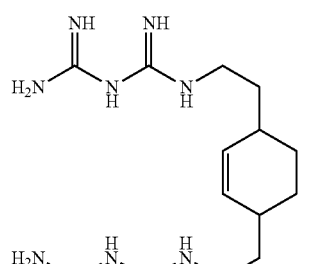
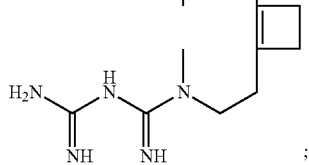
6
-continued
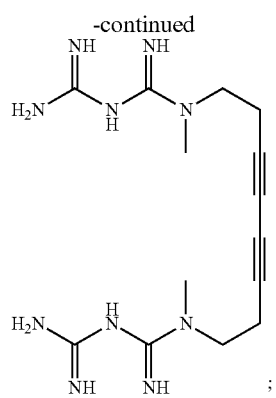
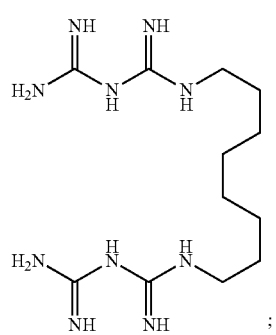
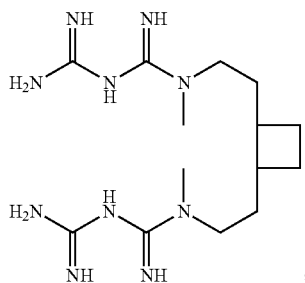
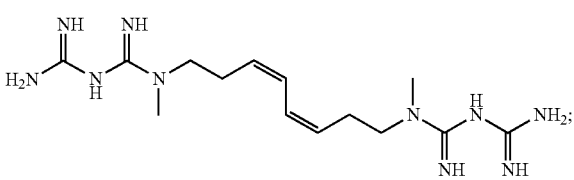
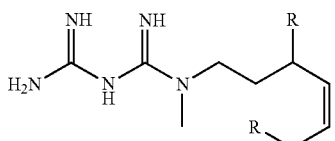
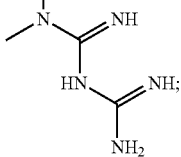

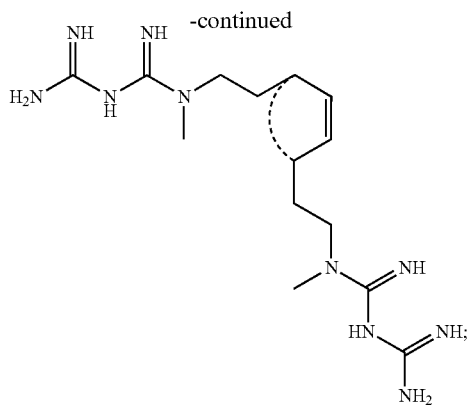

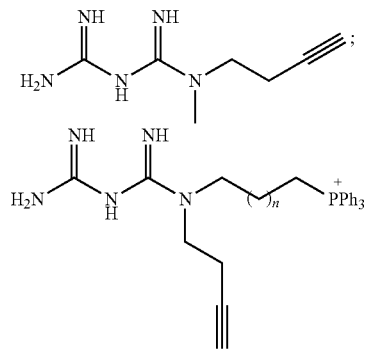

with n being an integer selected from 3 to 9; and

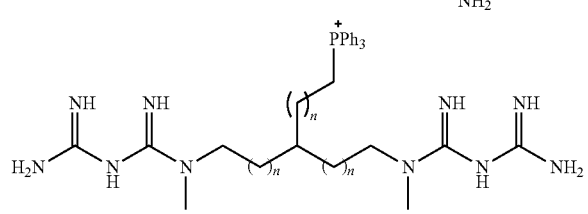

with n being independently an integer selected from 0 to 5;

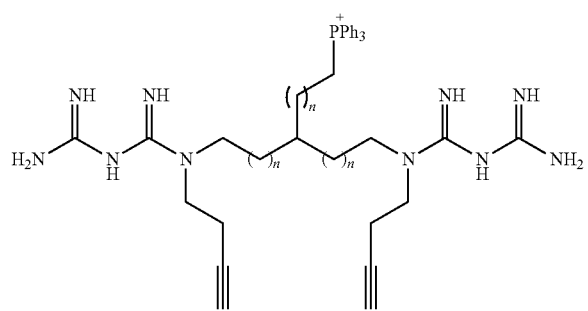

with n being independently an integer selected from 0 to 5, or a pharmaceutically acceptable salt thereof The present invention also relates to a conjugate comprising a compound as disclosed herein covalently linked to a drug, a toxin or a label. More particularly, it relates to a conjugate obtainable by reacting a compound according to the present disclosure having an alkyne group with a drug, a toxin or a label covalently linked to an azide ($N_3$) group.

It further relates to a pharmaceutical or veterinary composition comprising a compound or a conjugate as disclosed herein. Optionally, the pharmaceutical or veterinary composition further comprises another drug, preferably an antitumoral drug, more preferable a drug selecting from the group consisting of chemotherapeutics, anti-cancer antibodies, hormonal therapy, immunotherapy, kinase inhibitors and combinations thereof.

The present invention relates to a compound, a conjugate or a pharmaceutical composition as disclosed herein for use as a medicament, especially for treating cancer, for instance a cancer selected in the group consisting of rectal cancer, colorectal cancer, stomach cancer, head and neck cancer, thyroid cancer, cervical cancer, uterine cancer, breast cancer, in particular triple negative breast cancer, ovarian cancer, brain cancer, in particular glioblastoma and neuroblastoma, lung cancer, in particular small-cell lung cancer and non-small-cell lung cancer, skin cancer, bladder cancer, blood cancer, renal cancer, liver cancer, prostate cancer, multiple myeloma, and endometrial cancer. Optionally, the compound, conjugate or pharmaceutical composition is used in combination with radiotherapy and/or another drug, preferably an antitumoral drug, more preferable a drug selecting from the group consisting of chemotherapy, hormonotherapy and immunotherapy.

with n being independently an integer selected from 0 to 5; wherein
the dotted line being present or absent and being one or two atoms with covalent bonds; and
R is selected from the group consisting of a $C_1$-$C_6$ alkyl, a $C_1$-$C_6$ alkyloxy, a $C_1$-$C_6$ halogenoalkyl, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, the group being optionally substituted by a group R'; R' being selected from the group consisting of a $C_1$-$C_6$ alkyl, a $C_1$-$C_6$ alkyloxy, a $C_1$-$C_6$ thioalkyl, a halogen, a $C_1$-$C_6$ halogenoalkyl, a hydroxyl (—OH), a cyano (—CN), a nitro, an amino (—$NH_2$), a carboxyl (—COOH), a phosphate ($PO_4$), an amide (—$CONH_2$), —COOR″, —NHR″, —NR″R‴, —COR″, —CONHR″, —NHCOR″, —NHSO$_2$R″, —SOR″, —SO$_2$R″, —SONR″R‴, —SO$_2$NR″R‴, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, said cycloalkyl, cycloheteroalkyl, aryl or heteroaryl being optionally substituted by a halogen, a hydroxyl, a cyano, a nitro, an amino, or a $C_1$-$C_3$ alkoxy, with R″ and R‴ being H or a $C_1$-$C_6$ alkyl;
or a pharmaceutically acceptable salt thereof.

Optionally, the compound is selected from the group consisting of

Finally, the present invention relates to the use of a compound as disclosed herein and comprising an alkyne group for medical imaging or diagnosis.

DESCRIPTION OF THE DRAWINGS

(FIG. 1A) Molecular structures of metformin, phenformin and synthesis of metforminyn. (FIG. 1B) Dose response viability curves of cancer cells treated as indicated for 72 h. (FIG. 1C) Dose response viability curves of cells in epithelial and mesenchymal states of MDA-MB-468 cells treated as indicated for 72 h. (FIG. 1D) Dose response viability curves of HMLER cells in epithelial and mesenchymal states treated as indicated for 72 h. Data points and error bars, mean values and s.d. of three independent biological replicates.

(FIG. 2A) Schematic illustration of the labeling of metforminyn in cells using click chemistry. (FIG. 2B) Fluorescence microscopy images of labeled metforminyn. Cells were treated with metforminyn and subjected to click-labeling as described in Methods. Mitochondria were detected using cytochrome c immunostaining and 4',6-diamidino-2-phenylindole (DAPI) stains nuclear DNA. Scale bar, 10 µm. (FIG. 2C) Fluorescence microscopy detection of copper(II) in cancer cells treated as indicated for 48 h. Scale bar, 10 µm. (FIG. 2D) Flow cytometry analysis of copper(II) in cancer cells treated as indicated for 48 h. (FIG. 2E) Cyclic voltammetry measurements towards oxidation potentials (arrow) of a copper(I) solution. Data recorded in the absence and presence of metformin (2 mol equiv). Redox peak potentials are marked with dashed lines. (FIG. 2F) Flow cytometry analysis of iron(II) in cancer cells treated as indicated for 48 h. MDA-MB-468 cells were used in FIGS. 2C, D and D and were treated as described in Methods.

FIG. 4. Western blot and flow cytometry analyses of Ctr1 levels. MDA-MB-468 cells were treated as indicated for 72 h.

(FIG. 5A) Western blot analysis of levels of a mesenchymal marker (Vimentin), Ctr1 and copper-containing mitochondrial proteins (SOD1, Cox4) in cell treated with EGF for 72 h. (FIG. 5B) Flow cytometry analysis of Ctr1 protein level in cells treated with EGF for 72 h. (FIG. 5C) Flow cytometry analysis of copper(II) in cells treated with EGF for 72 h. (FIG. 5D) Western blot analysis of mesenchymal markers (Vimentin, Fibronectin) in cells treated as indicated for 72 h. (FIG. 5E) Fluorescence microscopy images of E-cadherin and Phalloidin in cells treated as indicated for 72 h. DAPI stains nuclear DNA. Scale bar, 10 µm. (FIG. 5F) Western blot analysis of mesenchymal markers and EMT-TF in cancer cells treated as indicated for 72 h. (FIG. 5G) Flow cytometry analysis of cells surface markers of cancer cells treated as indicated for 72 h and corresponding quantification. Bars and error bars, mean values and s.d. of three independent biological replicates. MDA-MB-468 cells were used throughout the figure.

DETAILED DESCRIPTION OF THE PRESENT INVENTION

Definitions

Figure 1:
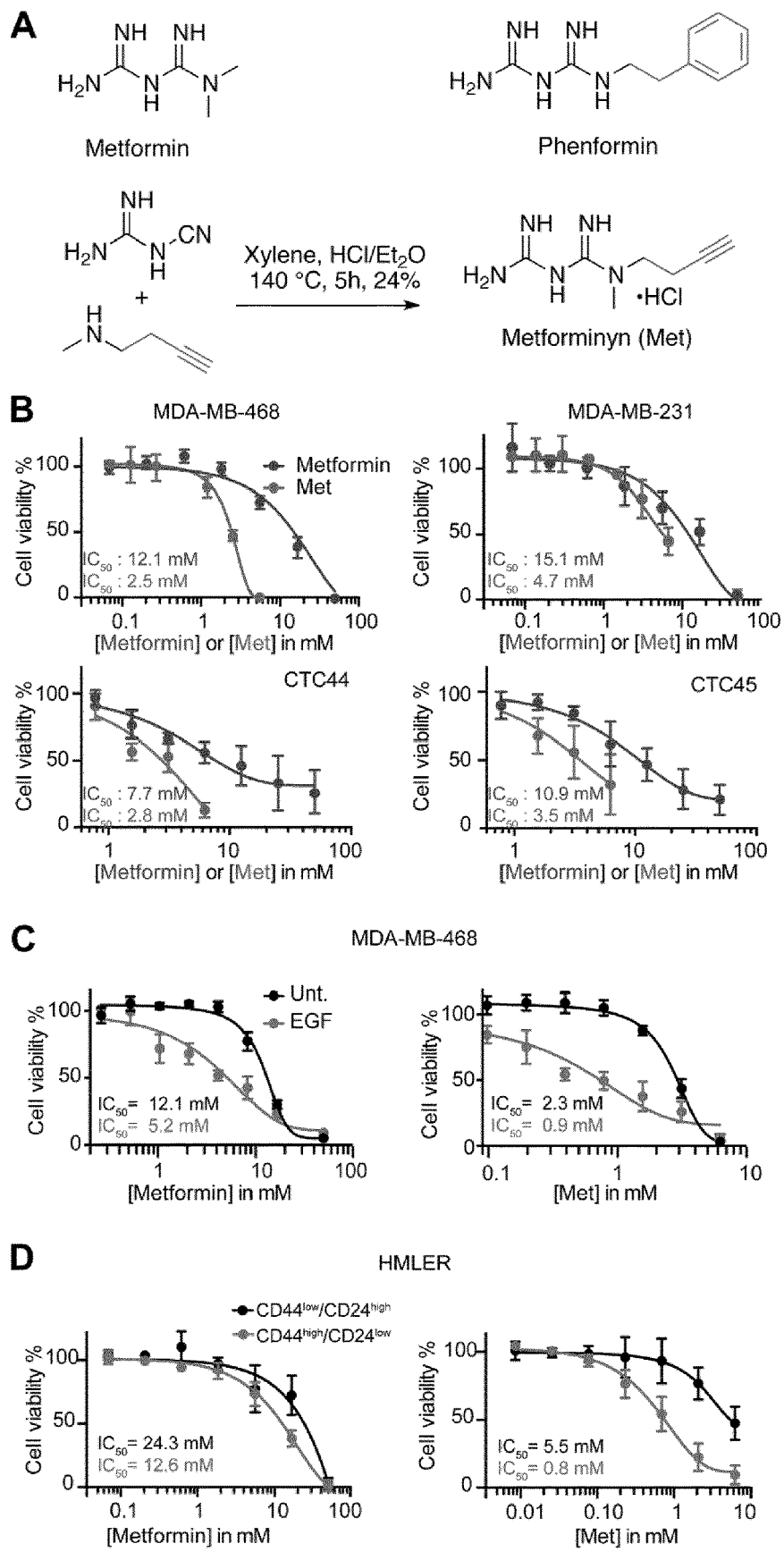
FIG. 1. Metformin and more potent compound metforminyn preferentially alter the proliferation of cancer cells in a mesenchymal state.

If, for example, the term $C_1$-$C_3$ is used, it means that the corresponding hydrocarbon chain may comprise from 1 to 3 carbon atoms, especially 1, 2 or 3 carbon atoms. If, for example, the term $C_1$-$C_6$ is used, it means that the corresponding hydrocarbon chain may comprise from 1 to 6 carbon atoms, especially 1, 2, 3, 4, 5 or 6 carbon atoms.

The term "alkyl" refers to a saturated, linear or branched aliphatic group. The term "($C_1$-$C_3$)alkyl" more specifically means methyl, ethyl, propyl, or isopropyl. The term "($C_1$-$C_6$)alkyl" more specifically means methyl, ethyl, propyl, isopropyl, butyl, isobutyl, tert-butyl, pentyl or hexyl. In a preferred embodiment, the "alkyl" is a methyl, an ethyl, a propyl, an isopropyl, or a tert-butyl, more preferably a methyl.

The term "alkoxy" or "alkyloxy" corresponds to the alkyl group as above defined bonded to the molecule by an —O-(ether) bond. ($C_1$-$C_3$)alkoxy includes methoxy, ethoxy, propyloxy, and isopropyloxy. ($C_1$-$C_6$)alkoxy includes methoxy, ethoxy, propyloxy, isopropyloxy, butyloxy, isobutyloxy, tert-butyloxy, pentyloxy and hexyloxy. In a preferred embodiment, the "alkoxy" or "alkyloxy" is a methoxy.

The term "thioalkyl" corresponds to the alkyl group as above defined bounded to the molecule by a —S-(thioether) bound. Thio-($C_1$-$C_6$)alkyl group includes thio-methyl, thio-ethyl, thio-propyl, thio-butyl, thio-pentyl and thio-hexyl.

The term "thioalkyl" corresponds to the alkyl group as above defined bounded to the molecule by a —S-(thioether) bound. Thio-($C_1$-$C_6$)alkyl group includes thio-methyl, thio-ethyl, thio-propyl, thio-butyl, thio-pentyl and thio-hexyl.

The term "heterocycloalkyl" corresponds to a saturated or unsaturated cycloalkyl group as above defined further comprising at least one heteroatom such as nitrogen, oxygen, or sulphur atom. It also includes fused, bridged, or spiro-connected heterocycloalkyl groups. Representative heterocycloalkyl groups include, but are not limited to 3-dioxolane, benzo[1,3]dioxolyl, pyrazolinyl, pyranyl, thiomorpholinyl, pyrazolidinyl, piperidyl, piperazinyl, 1,4-dioxanyl, imidazolinyl, pyrrolinyl, pyrrolidinyl, piperidinyl, imidazolidinyl, morpholinyl, 1,4-dithianyl, pyrrolidinyl, oxozolinyl, oxazolidinyl, isoxazolinyl, isoxazolidinyl, thiazolinyl, thiazolidinyl, isothiazolinyl, isothiazolidinyl, dihydropyranyl, tetrahydro-2H-pyranyl, tetrahydrofuranyl, and tetrahydrothiophenyl. The term "heterocycloalkyl" may also refer to a 5-10 membered bridged heterocyclyl such as 7-oxabicyclo[2,2,1]heptanyl. In a preferred embodiment, the heterocycloalkyl group is a tetrahydro-2H-pyranyl, a tetrahydro-2H-pyranyl, a tetrahydrothiophenyl, a morpholinyl, or a piperazinyl.

The term "aryl" corresponds to a mono-or bi-cyclic aromatic hydrocarbons having from 6 to 12 carbon atoms. For instance, the term "aryl" includes phenyl, biphenyl, or naphthyl. In a preferred embodiment, the aryl is a phenyl.

The term "heteroaryl" as used herein corresponds to an aromatic, mono-or poly-cyclic group comprising between 5 and 14 atoms and comprising at least one heteroatom such as nitrogen, oxygen or sulphur atom. Examples of such mono-and poly-cyclic heteroaryl group may be: pyridinyl, thiazolyl, thiophenyl, furanyl, pyrrolyl, pyrazolyl, imidazolyl, triazolyl, tetrazolyl, benzofuranyl, thianaphthalenyl, indolyl, indolinyl, quinolinyl, isoquinolinyl, benzimidazolyl, tetrahydroquinolinyl, tetrahydroisoquinolinyl, triazinyl, thianthrenyl, isobenzofuranyl, chromenyl, xanthenyl, phenoxanthinyl, isothiazolyl, isoxazolyl, pyrazinyl, pyridazinyl, indolizinyl, isoindolyl, indazolyl, purinyl, quinolizinyl, phtalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, indolinyl, isoindolinyl, oxazolidinyl, benzotriazolyl, benzisoxazolyl, oxindolyl, benzoxazolinyl, benzothienyl, benzothiazolyl, isatinyl, dihydropyridyl, pyrimidinyl, s-triazinyl, oxazolyl, or thiofuranyl. In a preferred embodiment, the heteroaryl group is a thiophenyl, a pyridinyl, a pyrazinyl, or a thiazolyl.

The term "halogen" corresponds to a fluorine, chlorine, bromine, or iodine atom, preferably a fluorine, chlorine or bromine, and more preferably a chlorine or a fluorine.

Within the context of the invention, the term treatment denotes curative, symptomatic, and preventive treatment. Pharmaceutical compositions, kits, products and combined preparations of the invention can be used in humans with existing cancer or tumor, including at early or late stages of progression of the cancer. The pharmaceutical compositions, kits, products and combined preparations of the invention will not necessarily cure the patient who has the cancer but will delay or slow the progression or prevent further progression of the disease, ameliorating thereby the patients' condition. In particular, the pharmaceutical compositions, kits, products and combined preparations of the invention reduce the development of tumors, reduce tumor burden, produce tumor regression in a mammalian host and/or prevent metastasis occurrence and cancer relapse. In treating the cancer, the pharmaceutical composition of the invention is administered in a therapeutically effective amount.

The term "cancer" or "tumor", as used herein, refers to the presence of cells possessing characteristics typical of cancer-causing cells, such as uncontrolled proliferation, and/or immortality, and/or metastatic potential, and/or rapid growth and/or proliferation rate, and/or certain characteristic morphological features. This term refers to any type of malignancy (primary or metastases) in any type of subject. In particular, the term encompasses prostate cancer at any stage of progression.

Whenever within this whole specification "treatment of a cancer" or the like is mentioned with reference to the pharmaceutical composition of the invention, there is meant: a) a method for treating a cancer, said method comprising administering a pharmaceutical composition of the invention to a subject in need of such treatment; b) the use of a pharmaceutical composition of the invention for the treatment of a cancer; c) the use of a pharmaceutical composition of the invention for the manufacture of a medicament for the treatment of a cancer; and/or d) a pharmaceutical composition of the invention for use in the treatment a cancer.

By "therapeutically effective amount" it is meant the quantity of the pharmaceutical composition of the invention which prevents, removes or reduces the deleterious effects of cancer in mammals, including humans, alone or in combination with the other active ingredients of the pharmaceutical composition, kit, product or combined preparation. It is understood that the administered dose may be lower for each compound in the composition to the "therapeutic effective amount" define for each compound used alone or in combination with other treatments than the combination described here. The "therapeutic effective amount" of the composition will be adapted by those skilled in the art according to the patient, the pathology, the mode of administration, etc.

As used herein, the term "antitumor chemotherapy" or "chemotherapy" refers to a cancer therapeutic treatment using chemical or biochemical substances, in particular using one or several antineoplastic agents. The term "hormonal therapy" refers to a cancer treatment having for purpose to block, add or remove hormones. For instance, in breast cancer, the female hormones estrogen and progesterone can promote the growth of some breast cancer cells. The term "immunotherapy" refers to a cancer therapeutic treatment using the immune system to reject cancer. The therapeutic treatment stimulates the patient's immune system to attack the malignant tumor cells.

Compounds

The present application discloses compounds having the formula (I):

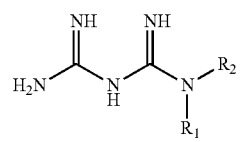

Formula (I)

wherein
R$_1$ is selected from the group consisting of H, a C$_1$-C$_6$ alkyl, preferably a C$_1$-C$_3$ alkyl, —(CH$_2$)$_a$—C≡CH, —(CH$_2$)$_b$—P$^+$Ph$_3$, a C$_3$-C$_{10}$ cycloalkyl, a C$_3$-C$_{10}$ cycloheteroalkyl, a C$_6$-C$_{12}$ aryl, and a C$_5$-C$_{12}$ heteroaryl, with "a" being an integer selected from 1 to 6, preferably 2 to 4, and "b" being an integer selected from 5 to 11, preferably 6 to 10, said alkyl, cycloalkyl, cycloheteroalkyl, aryl or heteroaryl being optionally substituted by a R group or a R' group;

R$_2$ is selected from the group consisting of
—(CH$_2$)$_d$—C≡CH, with "d" being an integer selected from 1 to 6;
—(CH$_2$)$_e$—CH=CH$_2$ with "e" being an integer selected from 2 to 6;
—(CH$_2$)$_f$—CR$_4$=CH—CH=CR$_5$—(CH$_2$)$_g$—R$_3$ with R$_4$ and R$_5$ being H, a R group or forming together a six-member ring, optionally substituted by one or two R' groups or fused with a cycloalkyl, an aryl, a cycloheteroalkyl or a heteroaryl having 3 to 6 members, "f" and "g" being an integer independently selected from 1 to 3;
—(CH$_2$)$_f$—C≡C—C≡C—(CH$_2$)$_g$—R$_3$, with "f" and "g" being an integer independently selected from 1 to 3;
—(CH$_2$)$_i$—R$_3$, with "i" being an integer selected from 7 to 9, preferably 8;
—(CH$_2$)$_j$—CH[(CH$_2$)$_k$—P+Ph$_3$]—(CH$_2$)$_l$—R$_3$ with "j" and "l" being integer independently selected from 1 to 6, and "k" being an integer selected from 1 to 6;
—(CH$_2$)$_m$-cyclobutanyl-(CH$_2$)$_n$—R$_3$ with "m" and "n" being an integer independently selected from 1 to 3; and
—(CH$_2$)$_p$—CHR$_6$—CH=CH—CHR$_7$—(CH$_2$)$_q$—R$_3$ with R$_6$ and R$_7$ being H, a R group or forming together a 4-6 member ring, optionally substituted by one or two R' groups or fused with a cycloalkyl, an aryl, a cycloheteroalkyl or a heteroaryl having 3 to 6 members, "p" and "q" being an integer independently selected from 1 to 3;

$R_3$ is

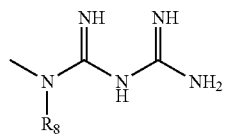

with $R_8$ selected from the group consisting of H, a $C_1$-$C_6$ alkyl, preferably a $C_1$-$C_3$ alkyl, —$(CH_2)_a$—C≡CH, —$(CH_2)_b$—$P^+Ph_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6, preferably 2 to 4, and "b" being an integer selected from 5 to 11, preferably 6 to 10, said alkyl, cycloalkyl, cycloheteroalkyl, aryl or heteroaryl being optionally substituted by a R group or a R' group; and R is selected from the group consisting of a $C_1$-$C_6$ alkyl, a $C_1$-$C_6$ alkyloxy, a $C_1$-$C_6$ halogenoalkyl, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, the group being optionally substituted by a group R', R' is selected from the group consisting of a $C_1$-$C_6$ alkyl, a $C_1$-$C_6$ alkyloxy, a $C_1$-$C_6$ thioalkyl, a halogen, a $C_1$-$C_6$ halogenoalkyl, a hydroxyl (—OH), a cyano (—CN), a nitro, an amino (—$NH_2$), a carboxyl (—COOH), a phosphate ($PO_4$), an amide (—$CONH_2$), —COOR", —NHR", —NR"R"', —COR", —CONHR", —NH-COR", —$NHSO_2R$", —SOR", —$SO_2R$", —SONR"R"', —$SO_2NR$"R"', a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, said cycloalkyl, cycloheteroalkyl, aryl or heteroaryl being optionally substituted by a halogen, a hydroxyl, a cyano, a nitro, an amino, or a $C_1$-$C_3$ alkoxy, with R" and R"' being H or a $C_1$-$C_6$ alkyl;

or a pharmaceutically acceptable salt thereof.

More particularly, the present invention related to new compounds having the formula (I):

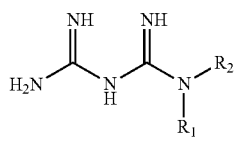

Formula (I)

wherein $R_1$ is selected from the group consisting of a $C_1$-$C_6$ alkyl, —$(CH_2)_a$—C≡CH, —$(CH_2)_b$—$P^+Ph_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6, preferably 2 to 4, and "b" being an integer selected from 5 to 11, preferably 6 to 10, said alkyl, cycloalkyl, cycloheteroalkyl, aryl or heteroaryl being optionally substituted by a R group or a R' group; and $R_2$ is selected from the group consisting of
—$(CH_2)_d$—C≡CH, with "d" being an integer selected from 1 to 6; and
—$(CH_2)_e$—CH=$CH_2$ with "e" being an integer selected from 2 to 6;

or $R_1$ is selected from the group consisting of H, a $C_1$-$C_6$ alkyl, —$(CH_2)_a$—C≡CH, —$(CH_2)_b$—$P^+Ph_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6, preferably 2 to 4, and "b" being an integer selected from 5 to 11, preferably 6 to 10, said alkyl, cycloalkyl, cycloheteroalkyl, aryl or heteroaryl being optionally substituted by a R group or a R' group;

$R_2$ is selected from the group consisting of
—$(CH_2)_f$—$CR_4$=CH—CH=$CR_5$—$(CH_2)_g$—$R_3$ with $R_4$ and $R_5$ being H, a R group or forming together a six-member ring, optionally substituted by one or two R' groups or fused with a cycloalkyl, an aryl, a cycloheteroalkyl or a heteroaryl having 3 to 6 members, "f" and "g" being an integer independently selected from 1 to 3;
—$(CH_2)_f$—C≡C—C≡C—$(CH_2)_g$—$R_3$, with "f" and "g" being an integer independently selected from 1 to 3;
—$(CH_2)_i$—$R_3$, with "i" being an integer selected from 7 to 9, preferably 8;
—$(CH_2)_j$—CH[$(CH_2)_k$—$P^+Ph_3$]—$(CH_2)_l$—$R_3$ with "j" and "l" being integer independently selected from 1 to 6, and "k" being an integer selected from 1 to 6;
—$(CH_2)_m$-cyclobutanyl-$(CH_2)_n$—$R_3$ with "m" and "n" being an integer independently selected from 1 to 3; and
—$(CH_2)_p$—$CHR_6$—CH=CH—$CHR_7$—$(CH_2)_q$—$R_3$ with $R_6$ and $R_7$ being H, a R group or forming together a 4-6 member ring, optionally substituted by one or two R' groups or fused with a cycloalkyl, an aryl, a cycloheteroalkyl or a heteroaryl having 3 to 6 members, "p" and "q" being an integer independently selected from 1 to 3; and $R_3$ is

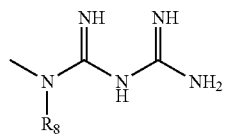

with $R_8$ selected from the group consisting of H, a $C_1$-$C_6$ alkyl, —$(CH_2)_a$—C≡CH, —$(CH_2)_b$—$P^+Ph_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6, preferably 2 to 4, and "b" being an integer selected from 5 to 11, preferably 6 to 10, said alkyl, cycloalkyl, cycloheteroalkyl, aryl or heteroaryl being optionally substituted by a R group or a R' group;

wherein

R is selected from the group consisting of a $C_1$-$C_6$ alkyl, a $C_1$-$C_6$ alkyloxy, a $C_1$-$C_6$ halogenoalkyl, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, the group being optionally substituted by a group R', R' is selected from the group consisting of a $C_1$-$C_6$ alkyl, a $C_1$-$C_6$ alkyloxy, a $C_1$-$C_6$ thioalkyl, a halogen, a $C_1$-$C_6$ halogenoalkyl, a hydroxyl (—OH), a cyano (—CN), a nitro, an amino (—$NH_2$), a carboxyl (—COOH), a phosphate ($PO_4$), an amide (—$CONH_2$), —COOR", —NHR", —NR"R"', —COR", —CONHR", —NH-COR", —$NHSO_2R$", —SOR", —$SO_2R$", —SONR"R"', —$SO_2NR$"R"', a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, said cycloalkyl, cycloheteroalkyl, aryl or heteroaryl being optionally substituted by a halogen, a hydroxyl, a cyano, a nitro, an amino, or a $C_1$-$C_3$ alkoxy, with R" and R'" being H or a $C_1$-$C_6$ alkyl;

or a pharmaceutically acceptable salt thereof.

In a first particular aspect, $R_1$ is selected from the group consisting of a methyl, —$(CH_2)_a$—C≡CH and —$(CH_2)_b$—$P^+Ph_3$, with "a" being an integer selected from 2 to 4, and "b" being an integer selected from 6 to 10; and.

$R_2$ is selected from the group consisting of
—$(CH_2)_d$—C≡CH, with "d" being an integer selected from 2 to 4; and
—$(CH_2)_e$—CH≡CH$_2$ with "e" being an integer selected from 2 to 6.

In a second particular aspect, $R_1$ is selected from the group consisting of H, a methyl, —$(CH_2)_a$—C≡CH and —$(CH_2)_b$—$P^+Ph_3$, with "a" being an integer selected from 2 to 4, and "b" being an integer selected from 6 to 10;

$R_2$ is selected from the group consisting of
—$(CH_2)_f$—$CR_4$=CH—CH=$CR_5$—$(CH_2)_g$—$R_3$ with $R_4$ and $R_5$ being H, "f" and "g" being an integer independently selected from 1 to 3, and "f"+"g" being from 2 to 4;
—$(CH_2)_f$—C≡C—C≡C—$(CH_2)_g$—$R_3$, with "f" and "g" being an integer independently selected from 1 to 3 and "f"+"g" being from 2 to 4;
—$(CH_2)_i$—$R_3$, with "i" being an integer selected from 7 to 9;
—$(CH_2)_j$—CH[$(CH_2)_k$—$P^+Ph_3$]—$(CH_2)_l$—$R_3$ with "j" and "l" being integer independently selected from 1 to 6, "j"+"l" being from 5 to 7, and "k" being an integer selected from 1 to 6;
—$(CH_2)_m$-cyclobutanyl-$(CH_2)_n$—$R_3$ with "m" and "n" being an integer independently selected from 1 to 3 and "m+n" being from 2 to 4; and
—$(CH_2)_p$—$CHR_6$—CH=CH—$CHR_7$—$(CH_2)_q$—$R_3$ with $R_6$ and $R_7$ being H or forming together a 4-member ring, "p" and "q" being an integer independently selected from 1 to 3 and "p"+"q" being from 2 to 4; and $R_3$ is

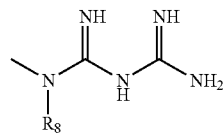

with $R_8$ selected from the group consisting of H, a methyl, $(CH_2)_a$—C≡CH and —$(CH_2)_b$—$P^+Ph_3$, with "a" being an integer selected from 1 to 6, preferably 2 to 4, and "b" being an integer selected from 5 to 11, preferably 6 to 10.

One particular aspect of the disclosure relates to compounds having at least one alkyne group (—C≡CH). One of the advantages of these compounds is that a terminal alkyne is suitable for labeling by means of click chemistry. Another advantage is based on the capacity of the alkyne group to chelate copper, in particular the mitochondrial copper.

Another particular aspect of the disclosure relates to compounds having two biguanidyl radicals. The advantage of increasing the number of biguanidyl radicals in the compound is that the copper chelation in particular of the mitochondrial copper, is increased and then the effect of the compounds on the cancer cells, especially cancer mesenchymal cells.

Finally, an aspect of the disclosure relates to compounds having both at least one alkyne group (—C≡CH) and two biguanidyl radicals. Compounds having both features are optimized for copper chelation, and then for the effect of the compounds on the cancer cells, especially cancer mesenchymal cells.

Compound With at Least One Alkyne Group

In one aspect, the compound has at least one alkyne group (—C≡CH). Optionally, the compound may have one, two, three or four alkyne groups. In this context, at least one among $R_1$, $R_2$ and $R_8$ is —$(CH_2)_a$—C≡CH with "a" being an integer from 1 to 6. "a" can be an integer selected from the group consisting of 1, 2, 3, 4, 5 and 6, or an integer from 2-6, 3-6, 4-6, 2-5, 3-5, 4-5, 2-4 or 2-3.

Optionally, both $R_1$ and $R_2$ are an alkyne group. Alternatively, either $R_1$ or $R_2$ is an alkyne group. Accordingly, the compound is of formula (I) with $R_1$ and $R_2$ being selected from the group consisting of H, a $C_1$-$C_6$ alkyl, —$(CH_2)_a$—C≡CH, —$(CH_2)_b$—$P^+Ph_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6, preferably 2 to 4, and "b" being an integer selected from 5 to 11, preferably 6 to 10, said alkyl, cycloalkyl, cycloheteroalkyl, aryl or heteroaryl being optionally substituted by a R group or a R' group and —$(CH_2)_e$—CH=CH$_2$ with "e" being an integer selected from 2 to 6; provided that at least one of $R_1$ and $R_2$ being —$(CH_2)_a$—C≡CH. Optionally, $R_1$ and $R_2$ are selected from the group consisting of H, a methyl, —$(CH_2)_a$—C≡CH and —$(CH_2)_b$—$P^+Ph_3$, provided that at least one of $R_1$ and $R_2$ being —$(CH_2)_a$—C≡CH.

Optionally, either $R_1$ or $R_2$ is an alkyne group and $R_8$ is an alkyne group, especially $R_1$ and $R_8$ are an alkyne group.

Accordingly, the compound is of formula (I) with $R_1$ being —$(CH_2)_a$—C≡CH;

$R_2$ is selected from the group consisting of
—$(CH_2)_f$—$CR_4$=CH—CH=$CR_5$—$(CH_2)_g$—$R_3$ with $R_4$ and $R_5$ being H, a R group or forming together a six-member ring, optionally substituted by one or two R' groups or fused with a cycloalkyl, an aryl, a cycloheteroalkyl or a heteroaryl having 3 to 6 members, "f" and "g" being an integer independently selected from 1 to 3;
—$(CH_2)_f$—C≡C—C≡C—$(CH_2)_g$—$R_3$, with "f" and "g" being an integer independently selected from 1 to 3;
—$(CH_2)_i$—$R_3$, with "i" being an integer selected from 7 to 9;
—$(CH_2)_j$—CH[$(CH_2)_k$—$P^+Ph_3$]—$(CH_2)_l$—$R_3$ with "j" and "l" being integer independently selected from 1 to 6, and "k" being an integer selected from 1 to 6;
—$(CH_2)_m$-cyclobutanyl-$(CH_2)_n$—$R_3$ with "m" and "n" being an integer independently selected from 1 to 3; and
—$(CH_2)_p$—$CHR_6$—CH=CH—$CHR_7$—$(CH_2)_q$—$R_3$ with $R_6$ and $R_7$ being H, a R group or forming together a 4-6 member ring, optionally substituted by one or two R' groups or fused with a cycloalkyl, an aryl, a cycloheteroalkyl or a heteroaryl having 3 to 6 members, "p" and "q" being an integer independently selected from 1 to 3;

R₃ is

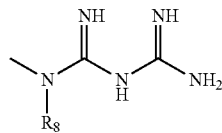

with R₈ being —(CH₂)ₐ—C≡CH.

Optionally, R₈ is an alkyne group and R₁ and R₂ are not an alkyne group.

Accordingly, the compound is of formula (I) with

R₁ is selected from the group consisting of H, a $C_1$-$C_6$ alkyl, —(CH₂)ᵦ—P⁺Ph₃, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "b" being an integer selected from 5 to 11, preferably 6 to 10, said alkyl, cycloalkyl, cycloheteroalkyl, aryl or heteroaryl being optionally substituted by a R group or a R' group;

R₂ is selected from the group consisting of
- —(CH₂)f—CR₄=CH—CH=CR₅—(CH₂)g—R₃ with R₄ and R₅ being H, a R group or forming together a six-member ring, optionally substituted by one or two R' groups or fused with a cycloalkyl, an aryl, a cycloheteroalkyl or a heteroaryl having 3 to 6 members, "f" and "g" being an integer independently selected from 1 to 3;
- —(CH₂)f—C≡C—C≡C—(CH₂)g—R₃, with "f" and "g" being an integer independently selected from 1 to 3;
- —(CH₂)ᵢ—R₃, with "i" being an integer selected from 7 to 9;
- —(CH₂)ⱼ—CH[(CH₂)ₖ—P⁺Ph₃]—(CH₂)ₗ—R₃ with "j" and "l" being integer independently selected from 1 to 6, and "k" being an integer selected from 1 to 6;
- —(CH₂)ₘ-cyclobutanyl-(CH₂)ₙ—R₃ with "m" and "n" being an integer independently selected from 1 to 3; and
- —(CH₂)ₚ—CHR₆—CH=CH—CHR₇—(CH₂)q—R₃ with R₆ and R₇ being H, a R group or forming together a 4-6 member ring, optionally substituted by one or two R' groups or fused with a cycloalkyl, an aryl, a cycloheteroalkyl or a heteroaryl having 3 to 6 members, "p" and "q" being an integer independently selected from 1 to 3;

R₃ is

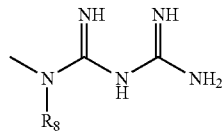

with R₈ being —(CH₂)ₐ—C≡CH.

Optionally, R₁ is selected from the group consisting of H, a methyl, —(CH₂)ₐ—C≡CH and —(CH₂)ᵦ—P⁺Ph₃

Optionally, R₂ is selected from the group consisting of
- —(CH₂)f—CR₄=CH—CH=CR₅—(CH₂)g—R₃ with R₄ and R₅ being H, a R group or forming together a six-member ring, optionally substituted by one or two R' groups or fused with a cycloalkyl, an aryl, a cycloheteroalkyl or a heteroaryl having 3 to 6 members, "f" and "g" being an integer independently selected from 1 to 3, and "f"+"g" being from 2 to 4;
- —(CH₂)f—C≡C—C≡C—(CH₂)g—R₃, with "f" and "g" being an integer independently selected from 1 to 3, and "f"+"g" being from 2 to 4;
- —(CH₂)ᵢ—R₃, with "i" being an integer selected from 7 to 9;
- —(CH₂)ⱼ—CH[(CH₂)ₖ—P⁺Ph₃]—(CH₂)ₗ—R₃ with "j" and "l" being integer independently selected from 1 to 6, and "j"+"l" being from 5 to 7 and "k" being an integer selected from 2 to 4;
- —(CH₂)ₘ-cyclobutanyl-(CH₂)ₙ—R₃ with "m" and "n" being an integer independently selected from 1 to 3, and "m+n" being from 2 to 4; and
- —(CH₂)ₚ—CHR₆—CH=CH—CHR₇—(CH₂)q—R₃ with R₆ and R₇ being H, a R group or forming together a 4-6 member ring, optionally substituted by one or two R' groups or fused with a cycloalkyl, an aryl, a cycloheteroalkyl or a heteroaryl having 3 to 6 members, "p" and "q" being an integer independently selected from 1 to 3, and "p"+"q" being from 2 to 4.

For instance, such compounds can be selected in the following group:

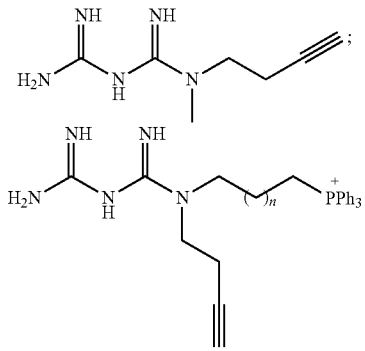

with n being an integer selected from 3 to 9, preferably from 4 to 8; and

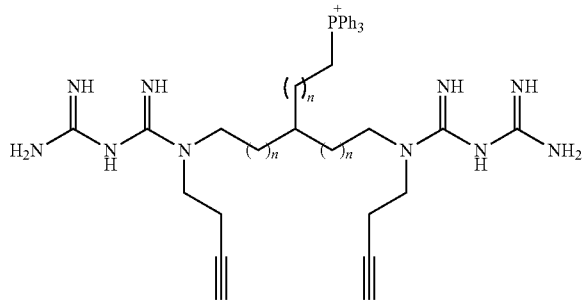

with n being independently an integer selected from 0 to 5, preferably from 1 to 3, and a pharmaceutically acceptable salt thereof.

Compounds Having Two Biguanidyl Radicals

In a second aspect that can be optionally combined with the first aspect, the compound has two biguanidyl radicals. In other words, R₃ is present in the compound.

Accordingly, the compounds of formula (I) are such that R₁ is selected from the group consisting of H, a $C_1$-$C_6$ alkyl, —(CH₂)ₐ—C≡CH, —(CH₂)ᵦ—P⁺Ph₃, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6, preferably 2 to 4, and "b" being an integer selected from 5 to 11, preferably 6 to 10, said alkyl, cycloalkyl, cycloheteroalkyl, aryl or heteroaryl being optionally substituted by a R group or a R' group; $R_2$ is selected from the group consisting of —$(CH_2)_f$—$CR_4$=CH—CH=$CR_5$—$(CH_2)_g$—$R_3$ with $R_4$ and $R_5$ being H, a R group or forming together a six-member ring, optionally substituted by one or two R' groups or fused with a cycloalkyl, an aryl, a cycloheteroalkyl or a heteroaryl having 3 to 6 members, "f" and "g" being an integer independently selected from 1 to 3;

—$(CH_2)_f$—C≡C—C≡C—$(CH_2)_g$—$R_3$, with "f" and "g" being an integer independently selected from 1 to 3;

—$(CH_2)_i$—$R_3$, with "i" being an integer selected from 7 to 9, preferably 8;

—$(CH_2)_j$—CH[$(CH_2)_k$—$P^+Ph_3$]—$(CH_2)_l$—$R_3$ with "j" and "l" being integer independently selected from 1 to 6, and "k" being an integer selected from 1 to 6;

—$(CH_2)_m$-cyclobutanyl-$(CH_2)_n$—$R_3$ with "m" and "n" being an integer independently selected from 1 to 3; and —$(CH_2)_p$—$CHR_6$—CH=CH—$CHR_7$—$(CH_2)_q$—$R_3$ with $R_6$ and $R_7$ being H, a R group or forming together a 4-6 member ring, optionally substituted by one or two R' groups or fused with a cycloalkyl, an aryl, a cycloheteroalkyl or a heteroaryl having 3 to 6 members, "p" and "q" being an integer independently selected from 1 to 3;

$R_3$ is

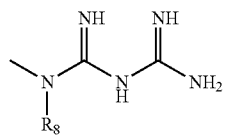

with Ro selected from the group consisting of H, a $C_1$-$C_6$ alkyl, —$(CH_2)_a$—C≡CH, —$(CH_2)_b$—$P^+Ph_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6, preferably 2 to 4, and "b" being an integer selected from 5 to 11, preferably 6 to 10, said alkyl, cycloalkyl, cycloheteroalkyl, aryl or heteroaryl being optionally substituted by a R group or a R' group.

Optionally, $R_1$ and $R_8$ are selected from the group consisting of H, a methyl, —$(CH_2)_a$—C≡CH and —$(CH_2)_b$—$P^+Ph_3$ Optionally, $R_2$ is selected from the group consisting of
—$(CH_2)_f$—$CR_4$=CH—CH=$CR_5$—$(CH_2)_g$—$R_3$ with $R_4$ and $R_5$ being H, a R group or forming together a six-member ring, optionally substituted by one or two R' groups or fused with a cycloalkyl, an aryl, a cycloheteroalkyl or a heteroaryl having 3 to 6 members, "f" and "g" being an integer independently selected from 1 to 3, and "f"+"g" being from 2 to 4;

—$(CH_2)_f$—C≡C—C≡C—$(CH_2)_g$—$R_3$, with "f" and "g" being an integer independently selected from 1 to 3, and "f"+"g" being from 2 to 4;

—$(CH_2)_i$—$R_3$, with "i" being an integer selected from 7 to 9;

—$(CH_2)_j$—CH[$(CH_2)_k$—$P^+Ph_3$]—$(CH_2)_l$—$R_3$ with "j" and "l" being integer independently selected from 1 to 6, and "j"+"l" being from 5 to 7 and "k" being an integer selected from 2 to 4;

—$(CH_2)_m$-cyclobutanyl-$(CH_2)_n$—$R_3$ with "m" and "n" being an integer independently selected from 1 to 3, and "m+n" being from 2 to 4; and —$(CH_2)_p$—$CHR_6$—CH=CH—$CHR_7$—$(CH_2)_q$—$R_3$ with $R_6$ and $R_7$ being H, a R group or forming together a 4-6 member ring, optionally substituted by one or two R' groups or fused with a cycloalkyl, an aryl, a cycloheteroalkyl or a heteroaryl having 3 to 6 members, "p" and "q" being an integer independently selected from 1 to 3, and "p"+"q" being from 2 to 4.

For instance, such compounds can be selected in the following group:

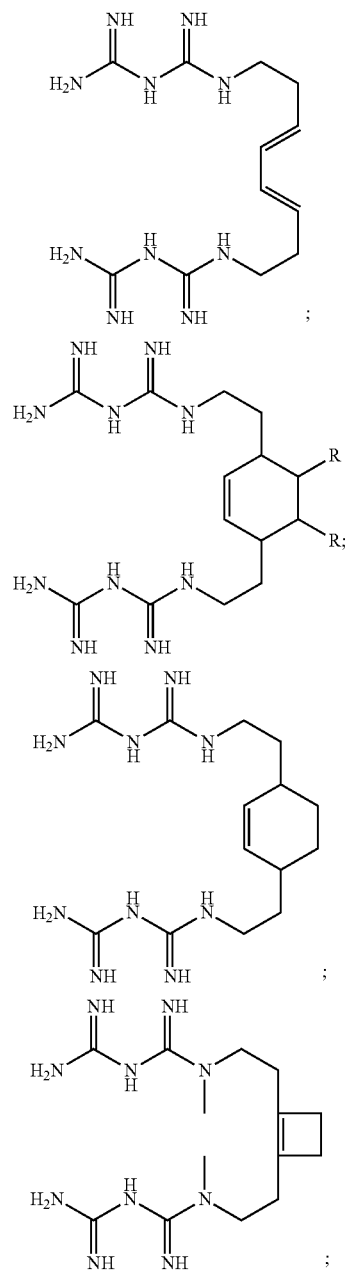

-continued

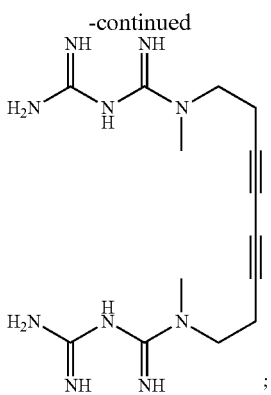

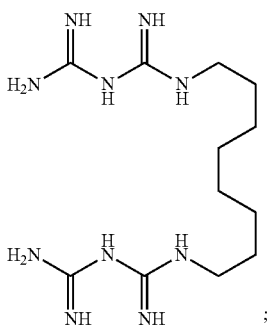

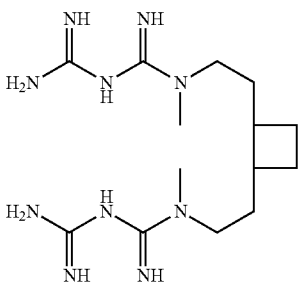

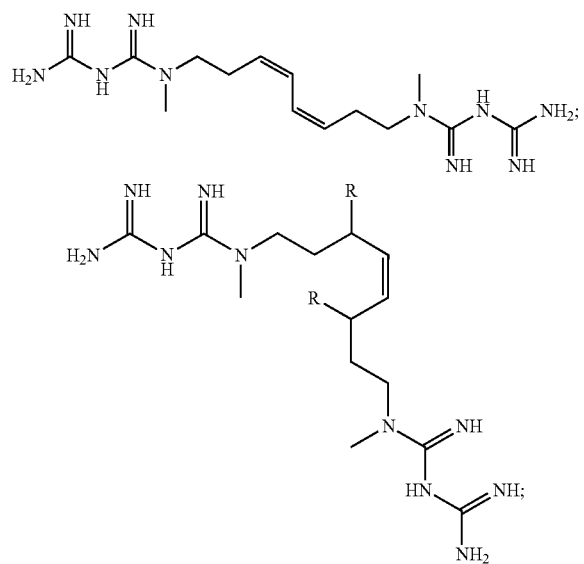

-continued

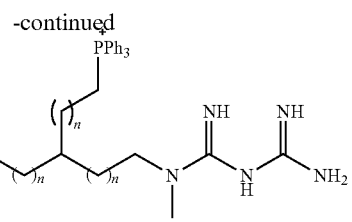

with n being independently an integer selected from 0 to 5, preferably from 1 to 3;

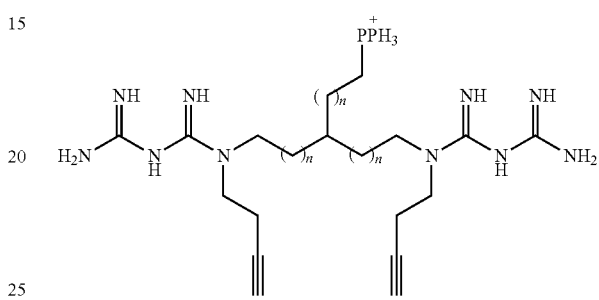

with n being independently an integer selected from 0 to 5, preferably from 1 to 3;

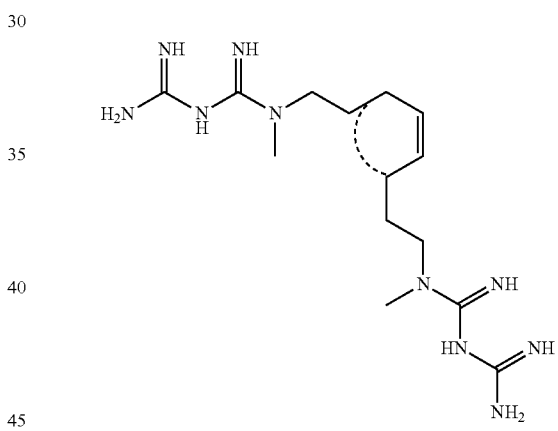

wherein
the dotted line being present or absent and being one or two atoms with covalent bonds; and
R is selected from the group consisting of a $C_1$-$C_6$ alkyl, a $C_1$-$C_6$ alkyloxy, a $C_1$-$C_6$ halogenoalkyl, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, the group being optionally substituted by a group R'; R' being selected from the group consisting of a $C_1$-$C_6$ alkyl, a $C_1$-$C_6$ alkyloxy, a $C_1$-$C_6$ thioalkyl, a halogen, a $C_1$-$C_6$ halogenoalkyl, a hydroxyl (—OH), a cyano (—CN), a nitro, an amino (—$NH_2$), a carboxyl (—COOH), a phosphate ($PO_4$), an amide (—$CONH_2$), —COOR'', —NHR'', —NR''R''', —COR'', —CONHR'', —NHCOR'', —$NHSO_2R''$, —SOR'', —$SO_2R''$, —SONR''R''', —$SO_2NR''R'''$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, said cycloalkyl, cycloheteroalkyl, aryl or heteroaryl being optionally substituted by a halogen, a hydroxyl, a cyano, a nitro, an amino, or a $C_1$-$C_3$ alkoxy, with R'' and R''' being H or a $C_1$-$C_6$ alkyl;
or a pharmaceutically acceptable salt thereof.

Compounds Having an Alkyne Group and Two Biguanidyl Radicals

In a particular aspect, the compounds have at least one alkyne group but also two biguanidyl radicals.

Accordingly, the compounds of formula (I) are such that.

$R_1$ is selected from the group consisting of H, a $C_1$-$C_6$ alkyl, —$(CH_2)_a$—C≡CH, —$(CH_2)_b$—$P^+Ph_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6, preferably 2 to 4, and "b" being an integer selected from 5 to 11, preferably 6 to 10, said alkyl, cycloalkyl, cycloheteroalkyl, aryl or heteroaryl being optionally substituted by a R group or a R' group;

$R_2$ is selected from the group consisting of
—$(CH_2)_f$—$CR_4$=CH—CH=$CR_5$—$(CH_2)_g$—$R_3$ with $R_4$ and $R_5$ being H, a R group or forming together a six-member ring, optionally substituted by one or two R' groups or fused with a cycloalkyl, an aryl, a cycloheteroalkyl or a heteroaryl having 3 to 6 members, "f" and "g" being an integer independently selected from 1 to 3;
—$(CH_2)_f$—C≡C—C≡C—$(CH_2)_g$—$R_3$, with "f" and "g" being an integer independently selected from 1 to 3;
—$(CH_2)_i$—$R_3$, with "i" being an integer selected from 7 to 9, preferably 8;
—$(CH_2)_j$—CH[$(CH_2)_k$—$P^+Ph_3$]—$(CH_2)_l$—$R_3$ with "j" and "l" being integer independently selected from 1 to 6, and "k" being an integer selected from 1 to 6;
—$(CH_2)_m$-cyclobutanyl-$(CH_2)_n$—$R_3$ with "m" and "n" being an integer independently selected from 1 to 3; and
—$(CH_2)_p$—$CHR_6$—CH=CH—$CHR_7$—$(CH_2)_q$—$R_3$ with $R_6$ and $R_7$ being H, a R group or forming together a 4-6 member ring, optionally substituted by one or two R' groups or fused with a cycloalkyl, an aryl, a cycloheteroalkyl or a heteroaryl having 3 to 6 members, "p" and "q" being an integer independently selected from 1 to 3;

$R_3$ is

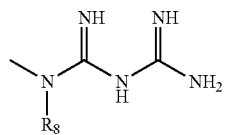

with $R_8$ selected from the group consisting of H, a $C_1$-$C_6$ alkyl, —$(CH_2)_a$—C≡CH, —$(CH_2)_b$—$P^+Ph_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6, preferably 2 to 4, and "b" being an integer selected from 5 to 11, preferably 6 to 10, said alkyl, cycloalkyl, cycloheteroalkyl, aryl or heteroaryl being optionally substituted by a R group or a R' group;

provided that at least one among $R_1$ and $R_8$ is —$(CH_2)_a$—C≡CH.

Optionally, $R_1$ and $R_8$ are selected from the group consisting of H, a methyl, —$(CH_2)_a$—C≡CH and —$(CH_2)_b$—$P^+Ph_3$ Optionally, $R_2$ is selected from the group consisting of
—$(CH_2)_f$—$CR_4$=CH—CH=$CR_5$—$(CH_2)_g$—$R_3$ with $R_4$ and $R_5$ being H, a R group or forming together a six-member ring, optionally substituted by one or two R' groups or fused with a cycloalkyl, an aryl, a cycloheteroalkyl or a heteroaryl having 3 to 6 members, "f" and "g" being an integer independently selected from 1 to 3, and "f"+"g" being from 2 to 4;
—$(CH_2)_f$—C≡C—C≡C—$(CH_2)_g$—$R_3$, with "f" and "g" being an integer independently selected from 1 to 3, and "f"+"g" being from 2 to 4;
—$(CH_2)_i$—$R_3$, with "i" being an integer selected from 7 to 9;
—$(CH_2)_j$—CH[$(CH_2)_k$—$P^+Ph_3$]—$(CH_2)_l$—$R_3$ with "j" and "l" being integer independently selected from 1 to 6, and "j"+"l" being from 5 to 7 and "k" being an integer selected from 2 to 4;
—$(CH_2)_m$-cyclobutanyl-$(CH_2)_n$—$R_3$ with "m" and "n" being an integer independently selected from 1 to 3, and "m+n" being from 2 to 4; and
—$(CH_2)_p$—$CHR_6$—CH=CH—$CHR_7$—$(CH_2)_q$—$R_3$ with $R_6$ and $R_7$ being H, a R group or forming together a 4-6 member ring, optionally substituted by one or two R' groups or fused with a cycloalkyl, an aryl, a cycloheteroalkyl or a heteroaryl having 3 to 6 members, "p" and "q" being an integer independently selected from 1 to 3, and "p"+"q" being from 2 to 4.

For instance, such a compound can be:

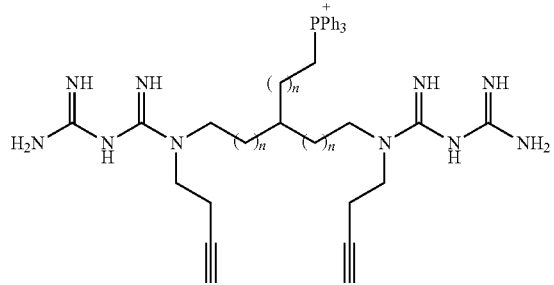

with n being independently an integer selected from 0 to 5, preferably from 1 to 3; or a pharmaceutically acceptable salt thereof.

The pharmaceutically acceptable salt of the compounds of the present invention can be for instance a salt with an acid selected from the group consisting of formic acid, acetic acid, propionic acid, lactic acid, butyric acid, isobutyric acid, trifluoroacetic acid, malic acid, malonic acid, fumaric acid, succinic acid, glutamic acid, tartaric acid, oxalic acid, citric acid, glycolic acid, glucuronic acid, ascorbic acid, benzoic acid, phtalic acid, salicylic acid, anthranilic acid, benzenesulfonic acid, p-toluensulfonic acid, methansulfonic acid, dichloroacetic acid, aminooxy acetic acid, hydrochloric acid, hydrobromic acid, sulfuric acid, phosphoric acid, nitric acid, carbonic acid, and boric acid.

Conjugate

The present invention relates to a conjugate comprising a compound of formula (I) as disclosed herein covalently linked to a toxin, a drug or a label. More particularly, it relates to a conjugate obtainable or obtained by reacting a compound according to the present disclosure having an alkyne group with a drug, a toxin or a label covalently linked to an azide ($N_3$) group.

As the compound of formula (I) has the capacity to target mitochondria, the toxin, drug or label is selected among the toxin or drug for which there is an interest to target specifically mitochondria. The drug can be an antidiabetic drug, an anticancer drug, an antiparasitic drug, an antiviral drug, an antiepileptic drug, an anesthetic drug, an anti-inflammatory drug and an antiarrhythmic drug. The drug can be inhibitors of mitochondrial respiratory chain complexes, uncouplers and ionophores, regulators of permeability transition pore, regulators of mitochondrial potassium channels, antioxidants, inhibitors of mitochondrial ATPase, apoptosis regulators and the like. For instance, a non-exhaustive list of drugs includes rotenone, antimycin A, myxothiazole, cyanide, dinitrophenol, valinomycin, nigericin, cyclosporin A, bongkrekic acid, betulinic acid, CD437,sangliferin, Ro 68-3400, atractyloside, protoporhyrin IX, diazoxide, pinacidil, nicorandil, cromakalim, glibenclamide, 5-HD, NS1619, NS004, CGS 7184, paxillline, IbTx, ChTx, oligomycin C, apoptolidin A, resveratrol, Bz-423, diindolyl-methane, aurovertin, PK11195, R207910, NSAIDs, minocycline, KB-R7943, dimebon, CoQ10, idebenone, lipoic acid, melatonin, vitamin E, nicotinamide, carnitine, L-carnitine, acetyl-L-carnitine, sirtuits, FK 506, deferoxamine, 3-bromopyruvate, 2-deoxyglucose, methyl jasmonate, mannoheptulose, gossypol. ABT-737, A-385358, ABT-263, HA14-1, AT-101, obatoclax, isothiocyanates, arsenictrioxide, lonidamide, arsenites, GSAO, clodronate, Ro5-4684, a-TOS, tamoxifen, piceatannol, rhodamine-123, dichloroacetate, CAP-232/TLN-232, MJE3, vitamin K3, fialuridine, 2-methoxyestradiol, b-lapachone, menadione, STA-4783, sanglifehrin, NIM811, Debio025, SSR180575, Ro5-4684; MitoSNO1, nitrite, mangafodipir, edaravone, statins, UQ, cariporide, propofol, MCI-186, pyruvate, minoxidil, a-lipolic acid, alda-1, etomoxir, perhexiline, ranolazine, trimetazidine, NAO, diazoside, BMS-191095, ascofuranone, nafuredin, atovaquone, flutolanil, atpenin A5, nafuredin-c (c-lactone derivative), thiazolidine-diones, fibrates, thizolidinediones, b-aminoisobutyric acid, SRT1720, trolox, ursodeoxycholic acid, doxorubicin, zidovudine, valproic acid, indomethacin, and carvedilol. In addition, the person skilled in the art has a good knowledge of drugs of interest as illustrated by Olszewska et al (IUBMB Life. 2013 March; 65(3):273-81).

In the context of cancer therapy, the conjugates of interest could be more particularly a conjugate of a compound of formula (I) with a drug selected from 3-bromopyruvate, 2-deoxyglucose, methyl jasmonate, mannoheptulose, gossypol. ABT-737, A-385358, ABT-263, HA14-1, AT-101, obatoclax, isothiocyanates, arsenictrioxide, lonidamide, arsenites, GSAO, clodronate, Ro5-4684, a-TOS, tamoxifen, piceatannol, rhodamine-123, dichloroacetate, CAP-232/TLN-232, MJE3, vitamin K3, fialuridine, 2-methoxyestradiol, b-lapachone, menadione, STA-4783, sanglifehrin, NIM811, Debio025, SSR180575, Ro5-4684; MitoSNO1, nitrite, and mangafodipir.

Optionally, the drug is an antitumoral agent, especially as disclosed below.

In one particular aspect, the conjugate can be prepared by the click chemistry using the alkyne group for the covalent link with the toxin, drug or label. The toxin, drug or label can be covalently linked to the azide ($N_3$) group and reacts with a compound of formula (I) having an alkyne group, especially by copper-catalyzed azide-alkyne cycloaddition (CuAAC). For a review concerning biorthogonal chemistry, including click-chemistry, one can refer to Sletten and Bertozzi, (Angew. Chem. Int. Ed. Engl. 2009, 48(38):6974-6998, the disclosure of which being incorporated herein by reference). The reaction of the alkyne with the azide is a [3+2] cycloaddition resulting in a triazole ring.

Label can be a directly or indirectly detectable moiety. The label can be selected among dyes, radiolabels and affinity tags. In particular, the dyes can be selected from the group consisting of fluorescent, luminescent or phosphorescent dyes, preferably dansyl, fluorescein, acridine, rhodamine, coumarin, BODIPY and cyanine dyes. More specifically, the fluorescent dyes can be selected among the dyes marketed by Thermo Fisher such as the Alexa Fluor dyes, Pacific dyes or Texas Red or by other providers for cyanines 3, 5 and 7. In particular, dyes bearing azide for CuAAC are commercially available for Alexa Fluor® 488, 55, 594 and 647 and for TAMRA (tetramethylrhodamine). In a second aspect, the label can be an affinity tag. Such an affinity tag can be for instance selected from the group consisting of biotin, His-tag, Flag-tag, strep-tag, sugars, lipids, sterols, PEG-linkers, and co-factors. In particular embodiment, the label is a biotinylated label. Biotins linked to azide are commercially available (Biotin azide). Finally, the label can be a radiolabel. It can be selected from the group consisting of radioactive forms of hydrogen, carbon, phosphorous, sulphur, and iodine, including tritium, carbon-11, carbon-14, phosphorous-32, phosphorous-33, sulphur-33, iodine-123, and iodine-125.

Pharmaceutical or Veterinary Composition

The present invention relates to a pharmaceutical or veterinary composition comprising a compound of formula (I) as disclosed herein or a conjugate comprising a compound of formula (I) as disclosed herein and a drug or toxin.

The pharmaceutical compositions contemplated herein may include a pharmaceutically acceptable carrier in addition to the active ingredient(s). The term "pharmaceutically acceptable carrier" is meant to encompass any carrier (e.g., support, substance, solvent, etc.) which does not interfere with effectiveness of the biological activity of the active ingredient(s) and that is not toxic to the host to which it is administered. For example, for parental administration, the active compounds(s) may be formulated in a unit dosage form for injection in vehicles such as saline, dextrose solution, serum albumin and Ringer's solution.

The pharmaceutical composition can be formulated as solutions in pharmaceutically compatible solvents or as emulsions, suspensions or dispersions in suitable pharmaceutical solvents or vehicle, or as pills, tablets or capsules that contain solid vehicles in a way known in the art. Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. Formulations suitable for parental administration conveniently comprise a sterile oily or aqueous preparation of the active ingredient which is preferably isotonic with the blood of the recipient. Every such formulation can also contain other pharmaceutically compatible and nontoxic auxiliary agents, such as, e.g. stabilizers, antioxidants, binders, dyes, emulsifiers or flavouring substances. The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof. The pharmaceutical compositions are advantageously applied by injection or intravenous infusion of suitable sterile solutions or as oral dosage by the digestive tract. Methods for the safe and effective administration of most of these chemotherapeutic agents are known to those skilled in the art. In addition, their administration is described in the standard literature.

The present invention relates to a compound of formula (I) as disclosed herein or a conjugate comprising a compound of formula (I) as disclosed herein and a drug or toxin for use as a drug, in particular for the treatment of a disease or disorder as defined below. It relates to the use of a compound of formula (I) as disclosed herein or a conjugate comprising a compound of formula (I) as disclosed herein and a drug or toxin for the manufacture of a drug, in particular for the treatment of a disease or disorder as defined below.

The compound of formula (I) as disclosed herein or a conjugate comprising a compound of formula (I) as disclosed herein and a drug or toxin can be used as a drug. In particular, it can be used for the treatment of a disease or disorder selected from non-exhaustive list including cancer, diabetes, in particular diabetes mellitus, obesity, hyperlipidemia, hypercholesterolemia, preeclampsia, liver and kidney diseases, in particular fatty liver, cardiovascular diseases, in particular coronary artery disease, osteoporosis, metabolic syndrome, multiple sclerosis, polycystic ovary disease, muscle pain, myocyte damage, rhabdomyolysis, erectile dysfunction, cognitive dysfunction, modulation of gut microbiota, neurodegenerative disorders and diseases such as Alzheimer's disease and Parkinson's disease, and as antiparasitic, antiviral, antiepileptic, anesthetic, anti-inflammatory and antiarrhythmic.

The pharmaceutical or veterinary composition as disclosed herein may further comprise an additional active ingredient or drug.

Cancer

In a particular aspect of the present invention, the compound of formula (I) as disclosed herein or a conjugate comprising a compound of formula (I) as disclosed herein and a drug or toxin is for use for treating cancer.

The terms "cancer", "cancerous", or "malignant" refer to or describe the physiological condition in mammals that is typically characterized by unregulated cell growth. Examples of cancer include, for example, leukemia, lymphoma, blastoma, carcinoma and sarcoma.

For instance, the cancer can be selected from the non-exhaustive list comprising rectal cancer, colorectal cancer, stomach cancer, head and neck cancer, thyroid cancer, cervical cancer, uterine cancer, breast cancer, in particular triple negative breast cancer, ovarian cancer, brain cancer, in particular glioblastoma and neuroblastoma, lung cancer, in particular small-cell lung cancer and non-small-cell lung cancer, skin cancer, bladder cancer, blood cancer, renal cancer, liver cancer, prostate cancer, multiple myeloma, and endometrial cancer. In a particular embodiment, the cancer can be selected from the list comprising pancreatic cancer, prostate cancer, liver cancer, cervical cancer; endometrial cancer, ovary cancer, breast cancer, colon cancer, glioblastoma, and neuroblastoma. In a very specific embodiment, the cancer can be selected from the list comprising ovary cancer, breast cancer, colon cancer, glioblastoma, and neuroblastoma. The cancer can be a mesenchymal ovarian cancer, in particular high grade ovarian cancer of the serous type, or an invasive breast cancer and/or its metastasis.

In a preferred embodiment, the cancer has mesenchymal cells. Indeed, the compounds of formula (I) as disclosed herein are able to selectively target the population of cancer cells with mesenchymal features. In a particular aspect, the compounds of formula (I) as disclosed herein present the advantage to act against circulating tumor cells, especially cancer stem cells.

Accordingly, the present invention relates to a compound of formula (I) as disclosed herein for use in the inhibition of cancer recurrence or cancer metastasis; and to a method for inhibit cancer recurrence or cancer metastasis by administering a compound as disclosed herein.

In a particular embodiment, the subject has a metastatic cancer. In another particular embodiment, the subject has a cancer resistant to conventional antitumoral agent. In an additional particular embodiment, the subject has a secondary tumor or a relapsed tumor.

The compound of formula (I) as disclosed herein can be used in combination with another drug. Accordingly, the present invention relates to

- a pharmaceutical composition comprising a compound of formula (I) as disclosed herein and another drug as defined herein, and optionally a pharmaceutically acceptable carrier, in particular for use in the treatment of cancer;
- a product or kit containing a compound of formula (I) as disclosed herein and another drug as defined herein as a combined preparation for simultaneous, separate or sequential use, in particular in the treatment of cancer;
- a combined preparation which comprises a compound of formula (I) as disclosed herein and another drug as defined herein for simultaneous, separate or sequential use, in particular in the treatment of cancer;
- a pharmaceutical composition comprising a compound of formula (I) as disclosed herein for the use in the treatment of cancer in combination with a treatment with another drug as defined herein and/or with radiotherapy;
- the use of a pharmaceutical composition comprising a compound of formula (I) as disclosed herein for the manufacture of a medicament for the treatment of cancer in combination with a treatment with another drug as defined herein and/or radiotherapy;
- the use of a pharmaceutical composition comprising a compound of formula (I) as disclosed herein and another drug as defined herein, and optionally a pharmaceutically acceptable carrier for the manufacture of a medicament for the treatment of cancer;
- a method for treating a cancer in a subject in need thereof, comprising administering an effective amount of a pharmaceutical composition comprising a) a compound of formula (I) as disclosed herein, b) another drug as defined herein, and a pharmaceutically acceptable carrier;
- a method for treating a cancer in a subject in need thereof, comprising administering an effective amount of a pharmaceutical composition comprising a compound of formula (I) as disclosed herein, and an effective amount of a pharmaceutical composition comprising another drug as defined herein; or
- a method for treating a cancer in a subject in need thereof, comprising administering an effective amount of a pharmaceutical composition comprising a compound of formula (I) as disclosed herein and another drug as defined herein.

The terms "kit", "product" or "combined preparation", as used herein, defines especially a "kit of parts" in the sense that the combination partners as defined above can be dosed independently or by use of different fixed combinations with distinguished amounts of the combination partners, i.e. simultaneously or at different time points. The parts of the kit of parts can then, e.g., be administered simultaneously or chronologically staggered, that is at different time points and with equal or different time intervals for any part of the kit of parts. The ratio of the total amounts of the combination partners to be administered in the combined preparation can be varied. The combination partners can be administered by the same route or by different routes.

Radiotherapy includes, but is not limited to, γ-rays, X-rays, and/or the directed delivery of radioisotopes to tumor cells. Other radiotherapies include microwaves and UV-irradiation. Other approaches to radiation therapy are also contemplated in the present invention.

The other drug can be selected from the non-exhaustive list including chemotherapy, an immune checkpoint inhibitor, hormonotherapy, and immunotherapy.

Chemotherapy may include an inhibitor of topoisomerases I or II, a DNA crosslinker, a DNA alkylating agent, an anti-metabolic agent and/or inhibitors of the mitotic spindles.

Inhibitors of topoisomerases I and/or II include, but are not limited to, etoposide, topotecan, camptothecin, irinotecan, amsacrine, intoplicine, anthracyclines such as doxorubicin, epirubicin, daunorubicin, idarubicin and mitoxantrone. Inhibitors of Topoisomerase I and II include, but are not limited to, intoplicine.

DNA crosslinkers include, but are not limited to, cisplatin, carboplatin and oxaliplatin.

Anti-metabolic agents block the enzymes responsible for nucleic acid synthesis or become incorporated into DNA, which produces an incorrect genetic code and leads to apoptosis. Non-exhaustive examples thereof include, without limitation, folic acid antagonists, pyrimidine analogs, purine analogs and adenosine deaminase inhibitors, and more particularly Methotrexate, Floxuridine, Cytarabine, 6-Mercaptopurine, 6-Thioguanine, Fludarabine phosphate, Pentostatin, 5-fluorouracil, gemcitabine and capecitabine.

Alkylating agents include, without limitation, nitrogen mustards, ethylenimine derivatives, alkyl sulfonates, nitrosoureas, metal salts and triazenes. Non-exhaustive examples thereof include Uracil mustard, Chlormethine, Cyclophosphamide (CYTOXAN(R)), Ifosfamide, Melphalan, Chlorambucil, Pipobroman, Triethylenemelamine, Triethylenethiophosphoramine, Busulfan, Carmustine, Lomustine, Fotemustine, cisplatin, carboplatin, oxaliplatin, thiotepa, Streptozocin, Dacarbazine, and Temozolomide.

Inhibitors of the mitotic spindles include, but are not limited to, paclitaxel, docetaxel, vinorelbine, larotaxel (also called XRP9881; Sanofi-Aventis), XRP6258 (Sanofi-Aventis), BMS-184476 (Bristol-Meyer-Squibb), BMS-188797 (Bristol-Meyer-Squibb), BMS-275183 (Bristol-Meyer-Squibb), ortataxel (also called IDN 5109, BAY 59-8862 or SB-T-101131; Bristol-Meyer-Squibb), RPR 109881A (Bristol-Meyer-Squibb), RPR 116258 (Bristol-Meyer-Squibb), NBT-287 (TAPESTRY), PG-paclitaxel (also called CT-2103, PPX, paclitaxel poliglumex, paclitaxel polyglutamate or Xyotax™), ABRAXANE® (also called Nab-Paclitaxel; ABRAXIS BIOSCIENCE), Tesetaxel (also called DJ-927), IDN 5390 (INDENA), Taxoprexin (also called docosahexanoic acid-paclitaxel; PROTARGA), DHA-paclitaxel (also called Taxoprexin®), and MAC-321 (WYETH). Also see the review of Hennenfent & Govindan (2006, Annals of Oncology, 17, 735-749).

The immune checkpoint inhibitor can be selected from the group consisting of an anti-CTLA-4 (cytotoxic T lymphocyte associated protein 4) therapies such as ipilimumab, PD-1 (programmed cell death protein 1) inhibitors such as nivolumab, pembrolizumab, or BGB-A317, PDL1 (programmed cell death ligand) inhibitors such as atezolizumab, avelumab, or durvalumab, LAG-3 (Lymphocyte-activation gene 3) inhibitors such as BMS-986016, TIM-3 (T-cell immunoglobulin and mucin-domain containing-3) inhibitors, TIGIT (T cell immunoreceptor with Ig and ITIM domains) inhibitors, BLTA (B- and T-lymphocyte attenuator) inhibitors, IDO1 inhibitors such as epacadostat, or a combination thereof.

The hormonotherapy includes for instance Tamoxifen, Fareston, Arimidex, Aromasin, Femara, Zoladex/Lupron, Megace, and Halotestin.

Imaging and Diagnosis

The compound of the formula (I) as disclosed herein having an alkyne group is suitable for forming in situ a detectable entity, then for labeling mitochondria. Indeed, by carrying the click chemistry, especially the copper-catalyzed azide-alkyne cycloaddition (CuAAC), a label having an azide ($N_3$) group can be covalently linked to the compound of the formula (I) as disclosed having an alkyne group.

The copper-catalyzed azide-alkyne cycloaddition (CuAAC) generally necessitates the presence of copper(I) catalyzer. However, as shown in the examples, the addition of copper is not necessary. Indeed, as the compound of the formula (I) as disclosed herein is specifically targeted and localized in the mitochondria and the natural mitochondrial abundance of endogenous copper was sufficient to promote labeling of the compounds of the invention in native conditions.

The present invention relates to a kit comprising a compound of the formula (I) as disclosed herein having an alkyne group and a label bearing an azide group. The label can as defined in the above section "Conjugate", preferably a fluorescent label or a biotinylated label.

The present invention also relates to the in vitro, ex vivo or in vivo use of a compound of the formula (I) as disclosed herein having an alkyne group or of a kit as described above as a research tool, in particular for visualizing mitochondria, for instance for medical imaging or diagnosis.

The present invention relates to an in vitro method for visualizing mitochondria in cells, the method comprising:
  contacting a cell with a compound of the formula (I) as disclosed herein having an alkyne group;
  contacting said cell with a label bearing an azide group, preferably a fluorescent label; and
  detecting the label in said cell, preferably the fluorescent label.

Preferably, before the step of contacting said cell with a label bearing an alkyne group, the cell is permeabilized and then fixed.

Further aspects and advantages of the present invention will be described in the following examples, which should be regarded as illustrative and not limiting.

EXAMPLES

The clinically approved drug metformin has been shown to selectively kill persister cancer cells through mechanisms that are not fully understood. To provide further mechanistic insights, the inventors developed a new compound that is more potent than metformin against a panel of cancer cells and that can be labeled in situ by means of click chemistry. This technology enabled the inventors to provide the first evidence of mitochondrial targeting with this class of drugs. A combination of fluorescence microscopy and cyclic voltammetry indicated that metformin and the new compound target mitochondrial copper, inducing the production of reactive oxygen species in this organelle, mitochondrial dysfunction and apoptosis. Importantly, this study revealed that mitochondrial copper is required for the maintenance of a mesenchymal state of human cancer cells and that metformin and the new compound can block the epithelial-tomesenchymal transition, a biological process that normally accounts for the genesis of persister cancer cells, through direct copper targeting.

Results

Development of a Novel Compound Which is Potent Clickable Metformin Derivative.

To provide further mechanistic insights, the inventors set out to develop a derivative of metformin that would allow for direct visualization of the subcellular sites of action of biguanide drugs. To this end, they synthesized an alkyne-containing analogue that has been named metforminyn (Met) (3) (FIG. 1A). This analogue was designed after metformin and phenformin, where distal methyl/benzyl substituents have been replaced by a terminal alkyne suitable for labeling in cells by means of click chemistry.

A comparative evaluation of metformin and metforminyn against a series of triple negative human breast cancer cells and circulating tumor cells (CTC) from patients with colorectal cancer showed that the synthetic analogue metforminyn exhibited a higher potency compared to metformin (FIG. 1B: IC50 of 2.5, 4.7, 2.8 and 3.5 mM for metforminyn in comparison to 12.1, 15.1, 7.7 and 10.9 mM for metformin, respectively).

Cancer cells can undergo phenotypic alterations reminiscent of that observed during normal embryogenic development, to acquire physical properties allowing these cells to detach from primary sites and give rise to distal secondary tumors. This process of epithelial-to-mesenchymal transition (EMT), can be artificially induced from normal epithelial mammary cells or triple negative breast cancer cells, leading to cells with a pronounced mesenchymal phenotype. It is noteworthy that cells able to adopt such a metastable state have been shown to be refractory to conventional chemotherapies. These persister cancer cells have thus been associated to cancer relapse.

Importantly, metforminyn was more potent compared to metformin in these models, exhibiting a higher toxicity against MDA-MB-468 triple negative breast cancer cells transiently induced into a mesenchymal state using epidermal growth factor (EGF) (FIG. 1C: IC50 of 12.6, 5.2, 0.8 and 0.9 mM for metforminyn in comparison to 24.3, 12.1, 5.5 and 2.3 mM for metformin, respectively). A similar trend was observed for HMLER CD44high/CD24low mesenchymal cells compared to their HMLER CD44low/CD24high epithelial counterpart (FIG. 1D). These data indicated that metforminyn is suitable for cell imaging studies.

Metformin Targets Mitochondrial Copper.

Figure 2:
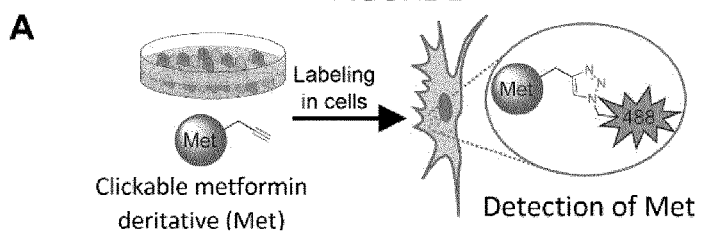
FIG. 2. Biguanides directly target mitochondria and promote copper oxidation.
Figure 2:
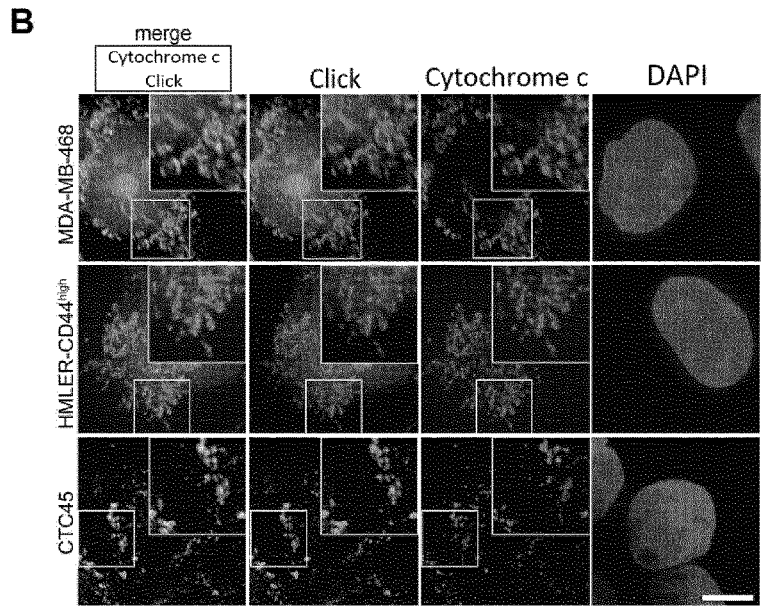
Figure 2:
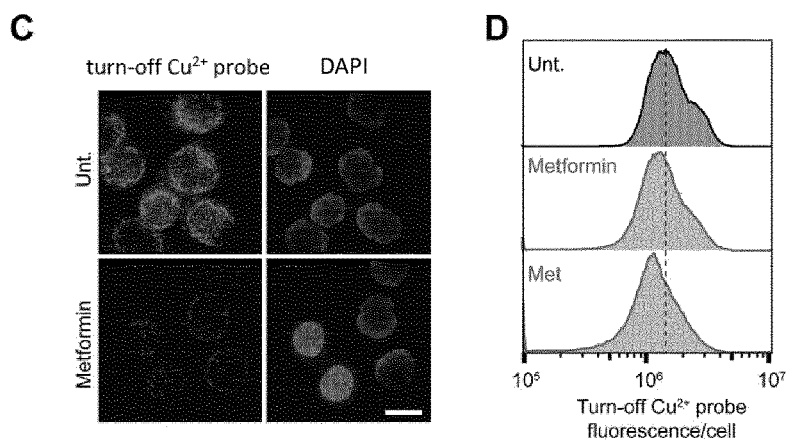
Figure 2:
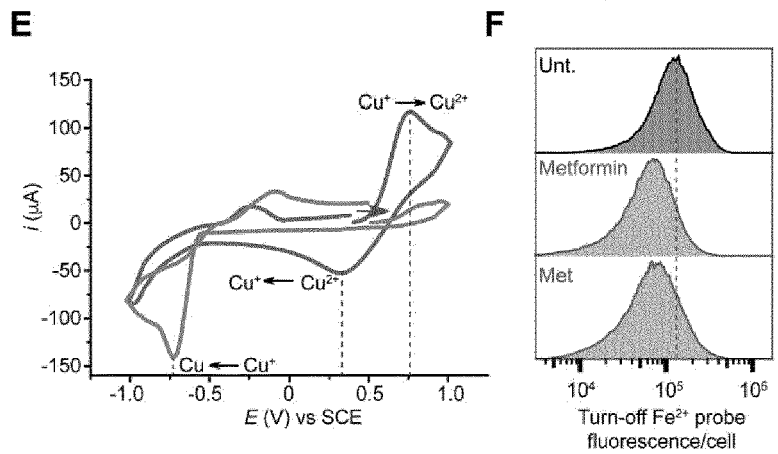
Figure 3A:
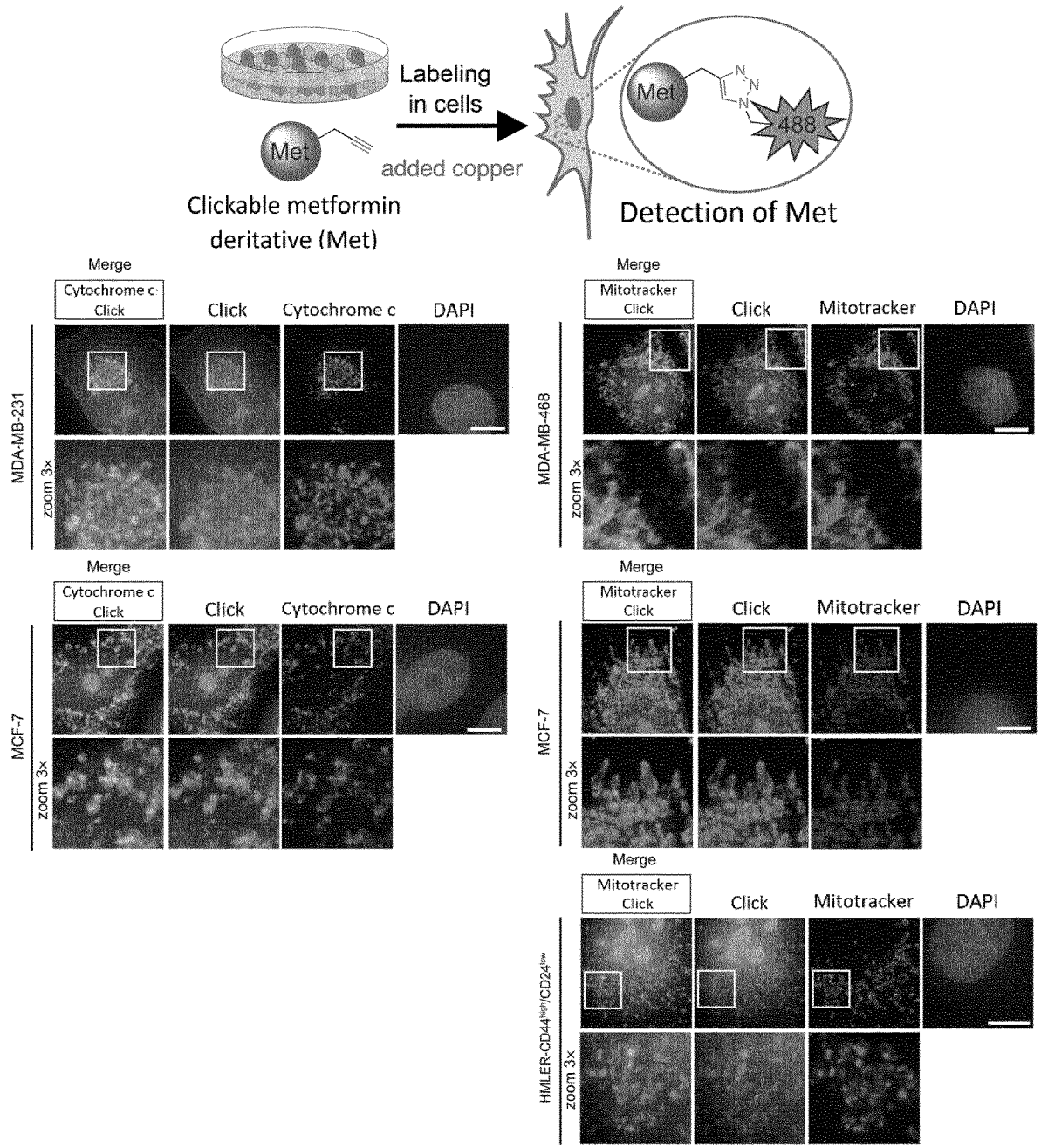
FIG. 3. Fluorescence microscopy imaging of labeled Met. The indicated cell lines were treated with Metforminyn and subjected to click-labeling. Metforminyn was labeled in cells as described in Methods with (FIG. 3A) or without (FIG. 3B) added copper catalyst. Mitochondria were detected using cytochrome c immunostaining or mitotracker, DAPI stains nuclear DNA. Scale bars, 10 µm. The terminology Cu-free indicates the absence of added copper catalyst on cells to promote labeling.

Cancer cells treated with metforminyn were subjected to labeling in cells by means of click chemistry to identify putative mechanistic sites of action of biguanides (FIG. 2A). In breast cancer cells, labeled metforminyn co-localized with cytochrome c, a cellular component that uniquely characterizes mitochondria, along with weaker nuclear staining and larger foci that resembled that observed for nucleolar proteins (FIG. 2B and FIG. 3A). In contrast, labeled metforminyn could not be detected in the nucleus of CTC that responded to treatment (FIG. 2B), consistent with the idea that mitochondria are functional targeted organelles of biguanides. Remarkably, labeling of metforminyn in cells, a chemical reaction that is normally catalyzed by copper(I), could be performed in situ without the need to incubate cells with additional copper catalyst (FIG. 3B). Thus, the natural mitochondrial abundance of endogenous copper was sufficient to promote labeling of metforminyn in native conditions. It further demonstrated that metforminyn chemically interacted with copper in this organelle.

This finding encouraged the inventors to investigate the effect of metformin and metforminyn on the mitochondrial levels of copper(II) using a selective turn-off fluorescent probe. Metformin and metforminyn induced a reduction in fluorescence of this turn-off probe in MDA-MB-468 cells indicating increased levels of copper(II) (FIGS. 2C and 2D). In addition, metformin altered the redox properties of copper as defined by the occurrence of cyclic voltammetry peaks characteristic of quasi-reversible couples (FIG. 2E), and treatment with metformin led to a reduced expression of the copper uptake protein 1 (Ctr1) in these cells (FIG. 4). These data indicated that increased levels of mitochondrial copper (II) occurred as a result of metformin directly interacting with, and promoting oxidation of copper(I) in this organelle rather than by increasing cellular uptake of copper. Interestingly, biguanide also increased levels of mitochondrial iron (II) as defined by flow cytometry using a selective turn-off probe (FIG. 2F) and cyclic voltammetry showed that metformin altered the redox properties of this metal suggesting a direct interaction. These data supported a model whereby metformin can directly inhibit complex I through iron binding, hijacking iron(III) from Fe—S clusters. Alternatively, iron(III) may also be consumed, acting as an electron scavenger of copper(I) oxidation upon treatment with metformin. Consistent with metformin acting as a pro-oxidant of copper in mitochondria and altering the ionic balance of copper and iron, treatment of MDA-MB-468 cells with metformin or metforminyn led to increased levels of reactive oxygen species (ROS) in this organelle accompanied by the reduction of mitochondrial membrane potentials and an alteration of mitochondrial morphology. Furthermore, cell death induced by metformin or metforminyn was rescued by the caspase 3 inhibitor Z-VAD-FMK but not the ferroptosis and necrosis inhibitors ferrostatin-1 and necrostatin-1, respectively, which was in line with apoptotic cell death taking place as a result of mitochondrial dysfunction.

Copper is an Essential Component of the Epithelial-To-Mesenchymal Transition.

The pronounced effect of metforminyn against mesenchymal cancer cells, accumulation of this biguanide in mitochondria and its effect on copper homeostasis in this organelle led the inventors to investigate a putative dependency of mesenchymal cancer cells on mitochondrial copper. Western blot analysis revealed that EGF-induced EMT led to a significant increase of mitochondrial copper-containing proteins including superoxide dismutase 1 (SOD1) and cytochrome c oxidase subunit 4 (Cox4), along with increased levels of Ctr1 and mitochondrial copper (FIG. 5A-C). Consistent with previous findings showing that mitochondrial load is higher in persister cancer cells, these data suggested that this cell state requires higher needs for energy production, a biological process that heavily relies on metalloproteins and metal co-factors essential to the mitochondrial ETC. Importantly, addition of copper synergized with EGF treatments to shift cancer cells toward a mesenchymal phenotype as defined by increased levels of mesenchymal markers (e.g. Vimentin, Fibronectin) and the proportion of cells harboring a CD44high/CD24low cell surface marker pattern (FIGS. 5D and 6).

Figure 5:
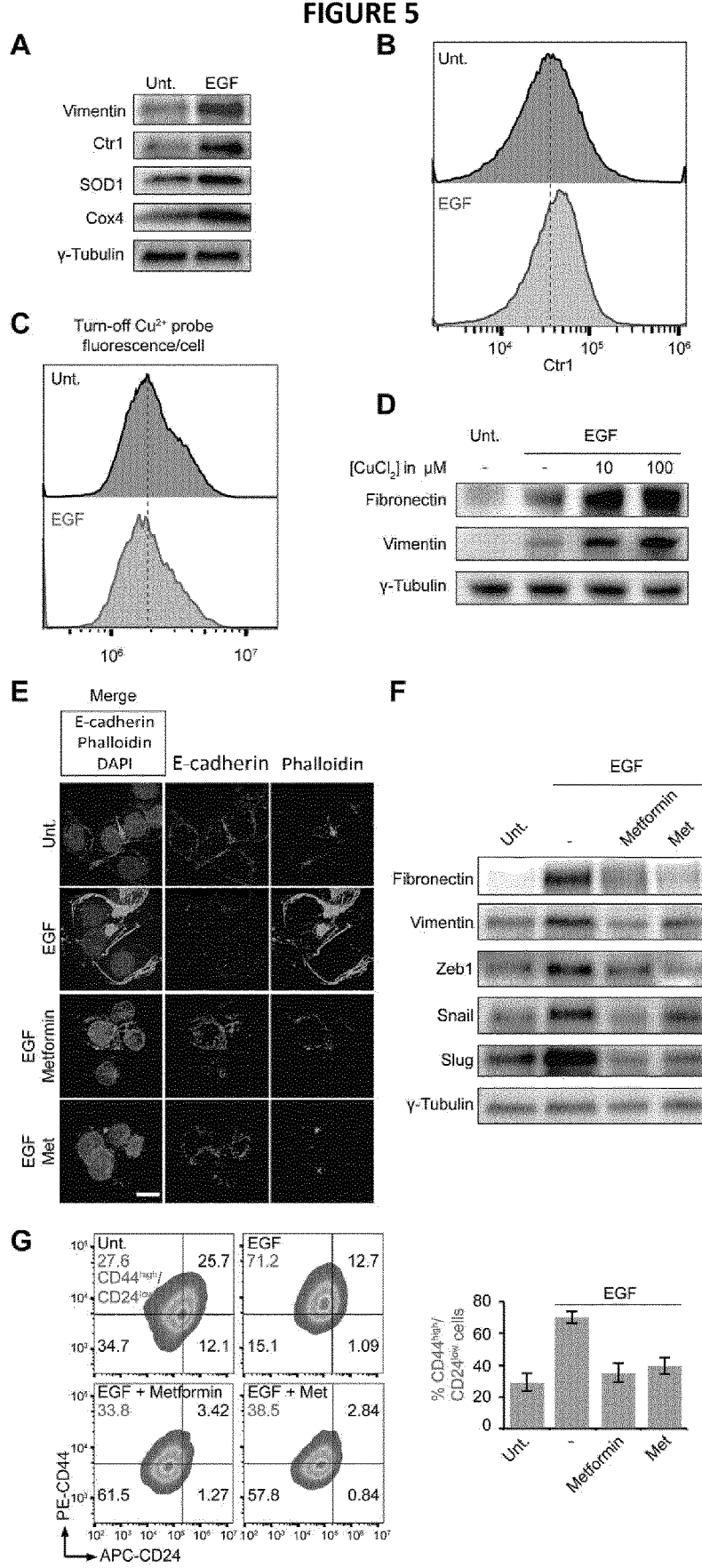
FIG. 5. Copper is required to maintain a mesenchymal state of cancer cells.
Figure 6:
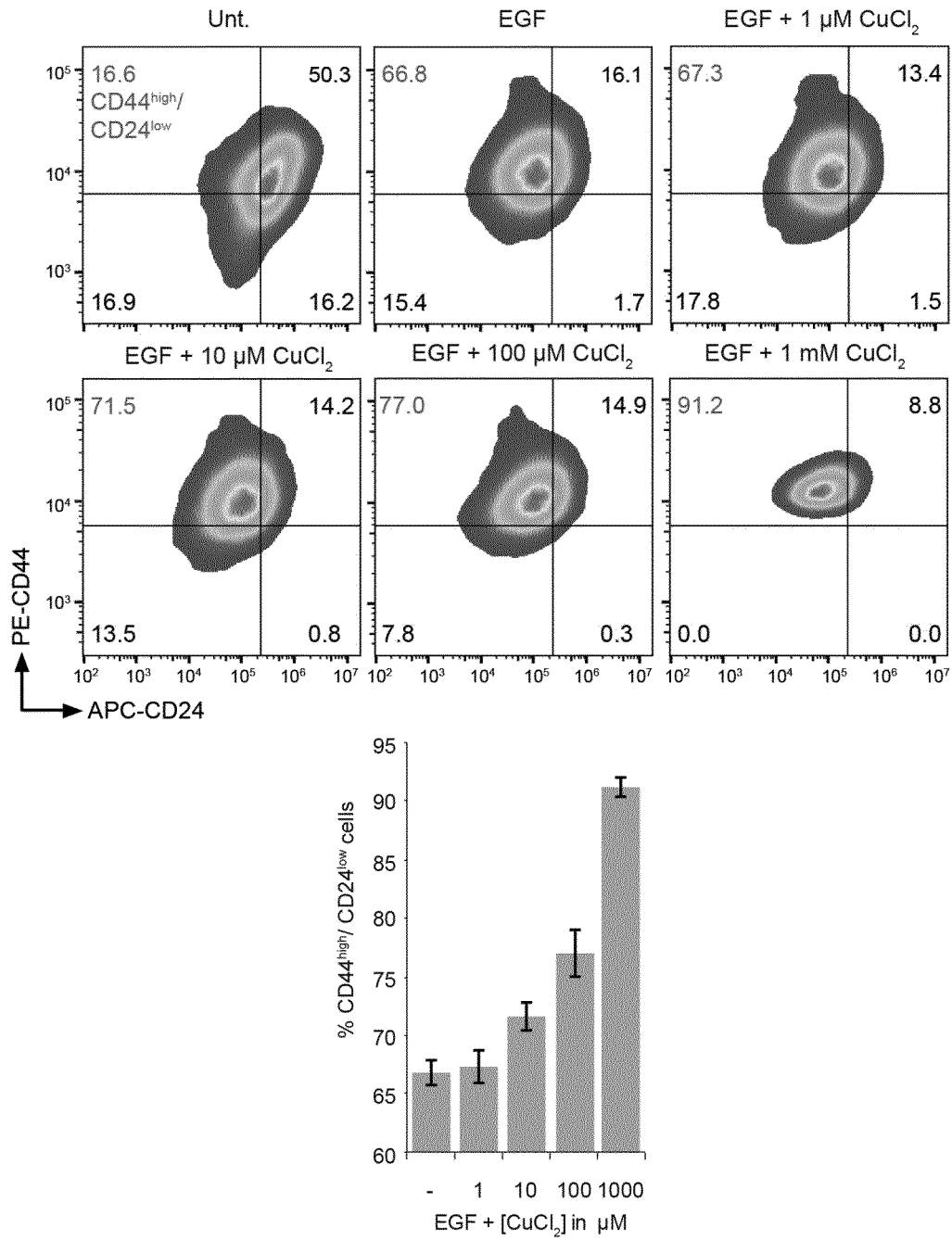
FIG. 6. Flow cytometry analysis of $CD44_{high}/CD24_{low}$ cells. MDA-MB-468 cells were treated with EGF and $CuCl_2$ as indicated for 72 h.

Finally, induction of EMT in MDA-MB-468 cells using EGF was prevented by metformin and metforminyn as defined by the subcellular localization of E-cadherin and phalloidin staining, levels of mesenchymal markers fibronectin, vimentin and EMT-transcription factors (TF) Zeb1, Snail and Slug as well as the proportion of cells harboring a CD44high/CD24low cell surface marker pattern (FIG. 5E-G). Altogether, these data revealed a dependency of mesenchymal cancer cells on mitochondrial copper, providing a rationale for the heightened sensitivity of these cells to biguanides.

Methods

Reagents. Copper chloride ($CuCl_2$, 459097, Sigma Aldrich), Ferrostatin-1 (Fer-1, SML0583, Sigma Aldrich, 10 µM for 72 h), human epidermal growth factor (EGF, 130-093-825, Miltenyi Biotech, 100 ng/ml for 96 h (plus 72 h for cell viability measurements), carbonyl cyanide mchlorophenylhydrazone (CCCP, 50 µM), Metformin (1,1-Dimethylbiguanide hydrochloride, J63361, Alfa Aesar, 12 mM unless stated otherwise), Metforminyn (Met, in-house drug, 2 mM unless stated otherwise), Necrostatin-1 (N9037, Sigma Aldrich, 20 µM for 72 h), Turn-off Cu(II) probe (10 µM for 1 h), Turn-off Fe(II) probe (1 µM for 1 h), Z-VAD-FMK (550377, BD Biosciences, 50 µM for 72 h).

Antibodies. Caspase 3 (9665S, Cell Signaling Technology, WB 1:500), CD24-APC (2155590, Sony Biotechnology Inc., FC 1:100), CD44-PE (FAB4948P, R&D Systems, FC 1:100), Copper uptake protein 1 (Ctr1, ab129067, Abcam, WB 1:1000 or FC 1:100), Cytochrome c (12963, Cell Signaling Technology, IF 1:500), Cytochrome c oxidase subunit 4 (Cox4, ab16056, Abcam, WB 1:2000), Ecadherin (20023195, Cell Signaling Technology, WB 1:1000), E-cadherin (610181, BD Biosciences, IF 1:200), Fibronectin (F0791, Sigma Aldrich, WB 1:1000), DyLight™ 488 Phalloidin (12935S, Cell Signaling Technology, IF 1:40), Slug (9585S, Cell Signaling Technology, WB 1:500), Snail (3895, Cell Signaling Technology, WB 1:500), Superoxide dismutase 1 (SOD1, ab13498, Abcam, WB 1:1000), γ-Tubulin (T5326, Sigma Aldrich, WB 1:2000), Vimentin (3932, Cell Signaling Technology, WB 1:500), Zeb1 (sc-81428, Santa Cruz Biotechnology, WB 1:500). Secondary antibodies for WB:HRP anti-Mouse (A90-116P, Bethyl Laboratories, WB 1:30000) and HRP anti-Rabbit (A120-108P, Bethyl Laboratories, 1:30000). Secondary antibodies for IF and FC: Alexa Fluor 488 conjugate (A-11017 Mouse, A-11008 Rabbit, Life Technologies, IF 1:500), Alexa Fluor 594 conjugate (A-11032 Mouse, A-11072 Rabbit, Life Technologies, IF 1:500), Alexa Fluor 647 conjugate (A-20991 Rabbit, A-20990 Mouse, Life Technologies, IF 1:500). All antibodies were diluted in blocking solution (2 or 5% BSA, 0.1% Tween-20/TBS).

Cell culture. Dulbecco's Phosphate-Buffered Saline (14190-094, 500 mL, Gibco), Dulbecco's Modified Eagle Medium (DMEM)/F12 (31331-028, 500 mL, Gibco), DMEM GlutaMAX™ (61965059, Thermo Fisher Scientific), Fetal Bovine Serum (FBS, 10270-106, Gibco), Hydrocortisone (H0888, Sigma Aldrich), Insulin (I0516 or I9278, Sigma Aldrich), PEN-STREP (DE17-602E, BioWhittaker, Lonza), Puromycin dihydrochloride (A11138-02, Life Technologies). MCF-7 (ATCC®, HTB-22™), MDA-MB-231 (ATCC®, HTB-26™), MDA-MB-468 (ATCC®, HTB-132™) and circulating tumor cells were grown in DMEM supplemented with 10% FBS and 1% penicillin (100 U/mL), streptomycin (100 µg/mL) and incubated at 37° C. with 5% $CO_2$. To induce EMT, cells were treated with epidermal growth factor EGF (100 ng/ml) (Miltenyi Biotec) for 72 h. The human mammary epithelial cell line infected with a retrovirus carrying hTERT, SV40 and the oncogenic allele HrasV12, named HMLER cells were a generous gift from A. Puisieux. HMLER cells were cultured in DMEM/F12 supplemented with 10% FBS, 10 µg/mL insulin, 0.5 µg/mL hydrocortisone, 10 ng/ml hEGF, and 0.5 µg/mL puromycin. A mycoplasma test was performed using PCR mycoplasma detection kit (G238, Applied Biological Materials).

Cell viability. Cell viability was carried out by plating 1000 cells/well in 96-well plates using CellTiter-Blue® viability assay according to the manufacturer's protocol. Cells were treated as indicated for 72 h. CellTiter-Blue® reagent (G8081, Promega) was added after 72 h treatment and cells were incubated for 1-2 h before recording fluorescence intensities (ex. 560/20 nm; em. 590/10 nm) using a Perkin Elmer Wallac 1420 Victor2 Microplate Reader.

Cell imaging. For immunofluorescence, cells were blocked with 2% BSA, 0.2% Tween-20/PBS (blocking buffer) for 20 min at RT. Cover-slips were incubated with 50 to 100 µL of diluted primary antibodies in blocking buffer 1 h at RT. Cover-slips were then washed three times with blocking buffer and incubated as described above with the appropriate secondary antibodies for 1 h. Cover-slips were washed three times with PBS and mounted using Vectashield Mounting Medium with DAPI (H-1200, VECTOR Laboratories). Fluorescence images were acquired using a Deltavision real-time microscope (Applied Precision). 60×/1.4NA and 100×/1.4NA objectives were used for 2D and 3D acquisitions that were deconvoluted with SoftWorx (Ratio conservative—15 iterations, Applied Precision) and processed with ImageJ®.

Chemical labeling of Met in cells. Cells were cultured at ~80% confluence and were treated with 0.3 mM Met for 3 h. Cell were fixed with formaldehyde (2% in PBS, 12 min) prior to permeabilization (Triton X-100, 0.1% in PBS, 5 to 10 min) and washed three times with 1% BSA/PBS. The click reaction cocktail was prepared from Click-iT® EdU Imaging kits (C10337, Life Technologies) according to the manufacturer's protocol. Briefly, mixing 430 µl of 1× Click-iT® reaction buffer with 20 µL of $CuSO_4$ solution, 1.2 µl Alexa Fluor® azide, 50 µl reaction buffer additive (sodium ascorbate) to reach a final volume of ~500 µL. Cover-slips were incubated with the click reaction cocktail in the dark at RT for 30 min, then washed three times with PBS. Immunofluorescence was then performed as indicated.

Western blotting. Cells were treated as indicated and then washed with PBS. Proteins were solubilized in Laemmli buffer containing benzonase (70664-3, VWR, 1:100) added. Extracts were incubated at 37° C. for 1 h. Proteins were resolved using pre-cast protein gels (Biorad) and a Trans-Blot® Turbo™ Transfer System (Biorad). Membranes were incubated with primary antibodies overnight in 5% FBS in PBS, 0.1% Tween-20. Primary antibodies were detected using horse-radishperoxidase (HRP) conjugated secondary antibodies (Jackson Laboratories) and the Super Signal enhanced chemiluminescent detection kit (Thermo Scientific). Signals were revealed using a Fusion Solo S Imaging System (Vilber).

Flow cytometry. Metal-specific probes were synthesized as previously described. Cells were treated as indicated in the figures. For mitochondrial copper and iron probes, cells were incubated with the relevant probe prior to being analyzed by flow cytometry. Cells were trypsinized and washed twice with ice cold PBS. For antibodies, cells were suspended in ice cold PBS containing 2% FBS and 1 mM EDTA (incubation buffer) and incubated for 20 min at 4° C. with the relevant antibody. Cells were then washed twice with ice cold PBS and suspended in incubation buffer prior to being analyzed by flow cytometry. For each condition, at least 100.000 cells were counted. Data were recorded on a BD Accuri™ C6 (BD Biosciences) and processed using Cell Quest (BD Biosciences) and FlowJo (FLOWJO, LLC) software.

Copper and iron levels. Cells were incubated with the relevant probes as described in Reagents section. Cells were then analyzed either by fluorescence microscopy or flow cytometry as described in Cell Imaging and Flow Cytometry sections.

Cyclic voltammetry. Cyclic voltammetry experiments were performed with a three-electrode cell under argon. Saturated Calomel Electrode (SCE) was used as reference, a steady Glassy Carbon (GC) electrode of diameter 3 mm was selected as working electrode and a Platinum wire as counterelectrode. All cyclic voltammograms were recorded at RT with a µ-autolab III from Metrohm using Nova software with a scan rate of 0.5 V/s. MeCN was used as a degassed HPLC grade from Carlo Erba. Water was mQ $H_2O$. Solutions with copper were prepared with 0.3 M $nBu_4NBF_4$ (180 mg) in MeCN (1.8 mL) and 200 µl of a 20 mM $Cu(MeCN)_4PF_6$ stock solution in MeCN (7.4 mg/mL). Then 20 L of a 400 mM metformin stock solution in mQ $H_2O$ (or PBS) (66.2 mg/mL) was added. Other MeCN solutions were prepared with 0.3 M $nBu_4NBF_4$ (200 mg) in MeCN (2 mL) and 20 µL of a 200 mM Fe $(NO_3)_3$ stock solution in mQ $H_2O$ (48.4 mg/ml), or/and 20 µl of a 400 mM metformin stock solution in mQ $H_2O$ (66.2 mg/1 mL). All aqueous solutions were prepared with 0.3 M $Na_2SO_4$ (85.2 mg) in mQ $H_2O$ (2 mL) and 20 µL of 200 mM $Fe(NO_3)_3$ stock solution in mQ $H_2O$ (48.4 mg/ml), or/and 20 µL of a 400 mM metformin stock solution in mQ $H_2O$ (66.2 mg/mL).

ROS levels. Mitochondrial ROS was measured using MitoSOX™ Red Mitochondrial Superoxide Indicator (M36008, Thermo Fisher Scientific) according to the manufacturer's protocol. In brief, cells were treated for the indicated time with the red fluorescent dye, trypsinized, washed and resuspended in ice cold PBS containing 2% FBS and 1 mM EDTA prior to being analyzed by flow cytometry.

Mitochondrial membrane potential. Measurements were performed using the MitoProbe™ JC-1 assay kit (M34152, Thermo Fischer Scientific) according to the manufacturer's protocol. In brief, cells were treated with 2 µM JC-1 or CCCP (m-chlorophenylhydrazone) control for the indicated time. Cells were then trypsinized, washed and resuspended in ice cold PBS containing 2% FBS and 1 mM EDTA prior to being analyzed by flow cytometry.

Cell death. Cells were treated as indicated in the figures. After treatment, cell death was quantified using Annexin V-FITC (A)/Propidium Iodide (PI) assay according to the manufacturer's protocol (Annexin V-FITC apoptosis detection kit II, 556570, BD Pharmingen™). Data were analyzed by a LSRFortessa™ flow cytometer (BD Biosciences, San Jose, CA) and processed using Cell Quest (BD Biosciences) and FlowJo (FLOWJO, LLC) software.

Chemical Synthesis

General information. All starting materials were purchased from commercial sources and used without further purification, or purified according to Purification of Laboratory Chemicals (Armarego, W. L. F., Chai, C. L. L. 5th edition). Reactions were monitored by thin-layer chromatography (TLC) using TLC silica gel coated aluminum plates 60F-254 (Merck). Metforminyn was purified using a Combiflash RF+Teledyne Isco system. $^1H$ NMR spectra were recorded at 300 MHz and $^{13}C$ NMR at 75 MHz at 298 K. Chemical shifts were reported as δ values are expressed in ppm using the residual non-deuterated solvent as internal standard and coupling constants (J) in Hz. The following abbreviations are used: s, singlet; t, triplet; td, triplet doublet. UPLC trace and electrospray mass spectrum were obtained from a Waters Acquity SQD2 UPLC-MS system. HRMS was measured with a Bruker maxis LC-QTOF.

Synthesis of metforminyn (Met). In a sealed tube, commercially available dicyandiamide (169 mg, 2.0 mmol) and N-methylbut-3-yn-1-amine (200 mg, 2.4 mmol) were suspended in 20 ml of xylene, then 2.5 mL of a 1M aq. HCl solution were added. The tube was closed and heated at 140° C. for 5 h. After this time, the reaction was cooled to RT and MeOH was added, then the solvent was removed under vacuum. The crude residue was purified by chromatography using a combiflash apparatus (DCM/MeOH, 10 to 20%) to afford metforminyn as a white solid (97 mg, 24%). $^1H$ NMR (300 MHz, MeOD) δ 3.60 (t, J=7.0 Hz, 1H), 3.09 (s, 1H), 2.50 (td, J=7.0, 3.0 Hz, 1H), 2.36 (t, J=3.0 Hz, 1H). $^{13}C$ NMR (75 MHz, MeOD) δ 160.8, 160.5, 81.9, 71.4, 50.3, 36.7, 18.3. HRMS (ESI-TOF) calculated for $C_7H_{14}N_5$ $[M+H]^+$ 168.1244, found 168.1246.

The invention claimed is:
1. A method for targeting mitochondrial copper, comprising the administration, to a subject in need thereof, of a compound of formula (I), a conjugate thereof or a pharmaceutical composition comprising said compound or conjugate, said conjugate comprising a drug or a toxin conjugated to an alkyne group in said compound via an azide ($N_3$) group, wherein compound of formula (I) is:

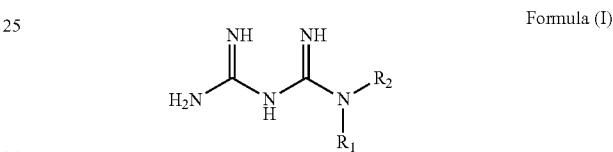

Formula (I)

wherein
$R_1$ is selected from the group consisting of a $C_1$-$C_6$ alkyl, —$(CH_2)_a$—C≡CH, —$(CH2)_b$—$P^+Ph_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6 and "b" being an integer selected from 5 to 11 said alkyl, cycloalkyl, cycloheteroalkyl, aryl or heteroaryl being optionally substituted by a R group or a R' group; and $R_2$ is selected from the group consisting of
—$(CH_2)_d$—C≡CH, with "d" being an integer selected from 1 to 6; and
—$(CH_2)_e$—CH=$CH_2$ with "e" being an integer selected from 2 to 6;

or
$R_1$ is selected from the group consisting of H, a $C_1$-$C_6$ alkyl, —$(CH_2)_a$—C≡CH, —$(CH_2)_b$—$P^+Ph_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6 and "b" being an integer selected from 5 to 11, said alkyl, cycloalkyl, cycloheteroalkyl, aryl or heteroaryl being optionally substituted by a R group or a R' group;

$R_2$ is selected from the group consisting of
—$(CH_2)_f$—$CR_4$=CH—CH=$CR_5$—$(CH_2)_g$—$R_3$ with $R_4$ and $R_5$ being H, a R group or forming together a six-member ring, optionally substituted by one or two R' groups or fused with a cycloalkyl, an aryl, a cycloheteroalkyl or a heteroaryl having 3 to 6 members, "f" and "g" being an integer independently selected from 1 to 3;
—$(CH_2)_f$—C≡C—C≡C—$(CH_2)_g$—$R_3$, with "f" and "g" being an integer independently selected from 1 to 3;
—$(CH_2)_i$—$R_3$, with "i" being an integer selected from 7 to 9;

—(CH$_2$)$_j$—CH[(CH$_2$)$_k$—P$^+$Ph$_3$]—(CH$_2$)$_l$—R$_3$ with "j" and "l" being integer independently selected from 1 to 6, and "k" being an integer selected from 1 to 6;

—(CH$_2$)$_m$-cyclobutanyl-(CH$_2$)$_n$—R$_3$ with "m" and "n" being an integer independently selected from 1 to 3; and —(CH$_2$)$_p$—CHR$_6$—CH=CH—CHR$_7$—(CH$_2$)$_q$—R$_3$ with R$_6$ and R$_7$ being H, a R group or forming together a 4-6 member ring, optionally substituted by one or two R' groups or fused with a cycloalkyl, an aryl, a cycloheteroalkyl or a heteroaryl having 3 to 6 members, "p" and "q" being an integer independently selected from 1 to 3; and R$_3$ is

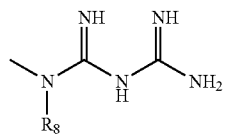

with R$_8$ selected from the group consisting of H, a C$_1$-C$_6$ alkyl, —(CH$_2$)$_a$—C≡CH, —(CH2)$_b$—P$^+$Ph$_3$, a C$_3$-C$_{10}$ cycloalkyl, a C$_3$-C$_{10}$ cycloheteroalkyl, a C$_6$-C$_{12}$ aryl, and a C$_5$-C$_{12}$ heteroaryl, with "a" being an integer selected from 1 to 6 and "b" being an integer selected from 5 to 11 said alkyl, cycloalkyl, cycloheteroalkyl, aryl or heteroaryl being optionally substituted by a R group or a R' group; and wherein R is selected from the group consisting of a C$_1$-C$_6$ alkyl, a C$_1$-C$_6$ alkyloxy, a C$_1$-C$_6$ halogenoalkyl, a C$_3$-C$_{10}$ cycloalkyl, a C$_3$-C$_{10}$ cycloheteroalkyl, a C$_6$-C$_{12}$ aryl, and a C$_5$-C$_{12}$ heteroaryl, the group being optionally substituted by a group R', R' is selected from the group consisting of a C$_1$-C$_6$ alkyl, a C$_1$-C$_6$ alkyloxy, a C$_1$-C$_6$ thioalkyl, a halogen, a C$_1$-C$_6$ halogenoalkyl, a hydroxyl (—OH), a cyano (—CN), a nitro, an amino (—NH$_2$), a carboxyl (—COOH), a phosphate (PO$_4^-$), an amide (—CONH$_2$), —COOR", —NHR"', —NR"R"', —COR", —CONHR", —NHCOR", —NHSO$_2$R", —SOR", —SO$_2$R", —SONR"R"', —SO2NR"R"', a C$_3$-C$_{10}$ cycloalkyl, C$_3$-C$_{10}$ cycloheteroalkyl, a C$_6$-C$_{12}$ aryl, and a C$_5$-C$_{12}$ heteroaryl, said cycloalkyl, cycloheteroalkyl, aryl or heteroaryl being optionally substituted by a halogen, a hydroxyl, a cyano, a nitro, an amino, or a C$_1$-C$_3$ alkoxy, with R" and R"' being H or a C$_1$-C$_6$ alkyl;

or a pharmaceutically acceptable salt thereof.

2. The method of claim 1, wherein the subject has a disease or a disorder selected from the group consisting of: cancer, diabetes, diabetes mellitus, obesity, hyperlipidemia, hypercholesterolemia, preeclampsia, liver and kidney diseases, fatty liver, cardiovascular diseases, coronary artery disease, osteoporosis, metabolic syndrome, multiple sclerosis, polycystic ovary disease, muscle pain, myocyte damage, rhabdomyolysis, erectile dysfunction, cognitive dysfunction, modulation of gut microbiota, neurodegenerative disorders and diseases, Alzheimer's disease, and Parkinson's disease.

3. The method of claim 2, wherein the subject has a cancer.

4. The method of claim 3, wherein the subject has a cancer with mesenchymal cells.

5. The method of claim 1, wherein the subject has a cancer selected from the group consisting of rectal cancer, colorectal cancer, stomach cancer, head and neck cancer, thyroid cancer, cervical cancer, uterine cancer, breast cancer, triple negative breast cancer, ovarian cancer, brain cancer, glioblastoma, neuroblastoma, lung cancer, small-cell lung cancer, non-small-cell lung cancer, skin cancer, bladder cancer, blood cancer, renal cancer, liver cancer, prostate cancer, multiple myeloma, and endometrial cancer.

6. The method of claim 1, for treating a disease or a disorder selected from the group consisting of: cancer, diabetes, diabetes mellitus, obesity, hyperlipidemia, hypercholesterolemia, preeclampsia, liver and kidney diseases, fatty liver, cardiovascular diseases, coronary artery disease, osteoporosis, metabolic syndrome, multiple sclerosis, polycystic ovary disease, muscle pain, myocyte damage, rhabdomyolysis, erectile dysfunction, cognitive dysfunction, modulation of gut microbiota, neurodegenerative disorders and diseases, Alzheimer's disease, and Parkinson's disease.

7. The method of claim 1, for treating cancer.

8. The method of claim 7, for treating a cancer with mesenchymal cells.

9. The method of claim 8, for treating a cancer selected from the group consisting of rectal cancer, colorectal cancer, stomach cancer, head and neck cancer, thyroid cancer, cervical cancer, uterine cancer, breast cancer, triple negative breast cancer, ovarian cancer, brain cancer, glioblastoma, neuroblastoma, lung cancer, small-cell lung cancer, non-small-cell lung cancer, skin cancer, bladder cancer, blood cancer, renal cancer, liver cancer, prostate cancer, multiple myeloma, and endometrial cancer.

10. The method of claim 1, further comprising treatment comprising radiotherapy chemotherapy, hormonotherapy or immunotherapy.

11. The method of claim 1, wherein R$_3$ is present in the compound.

12. The method of claim 1, wherein R$_2$ is selected from the group consisting of —(CH$_2$)$_d$—C≡CH, with "d" being an integer selected from 2 to 4;

—(CH$_2$)$_e$—CH—CH$_2$ with "e" being an integer selected from 2 to 4;

—(CH$_2$)$_f$—CR$_4$=CH—CH=CR$_5$—(CH$_2$)$_g$—R$_3$ with R$_4$ and R$_5$ being H, a R group or forming together a six-member ring, optionally substituted by one or two R' groups or fused with a cycloalkyl, an aryl, a cycloheteroalkyl or a heteroaryl having 3 to 6 members, "f" and "g" being an integer independently selected from 1 to 3, and "f"+"g" being from 2 to 4;

—(CH$_2$)$_f$—C≡C—C≡C—(CH$_2$)$_g$—R$_3$, with "f" and "g" being an integer independently selected from 1 to 3, and "f"+"g" being from 2 to 4;

—(CH$_2$)$_i$—R$_3$, with "i" being an integer selected from 7 to 9;

—(CH$_2$)$_j$—CH[(CH$_2$)$_k$—P$^+$Ph$_3$]—(CH$_2$)$_l$—R$_3$ with "j" and "l" being integer independently selected from 1 to 6, and "j"+"l" being from 5 to 7 and "k" being an integer selected from 2 to 4;

—(CH$_2$)$_m$-cyclobutanyl-(CH$_2$)$_n$—R$_3$ with "m" and "n" being an integer independently selected from 1 to 3, and "m+n" being from 2 to 4; and —(CH$_2$)$_p$—CHR$_6$—CH=CH—CHR$_7$—(CH$_2$)$_q$—R$_3$ with R$_6$ and R$_7$ being H, a R group or forming together a 4-6 member ring, optionally substituted by one or two R' groups or fused with a cycloalkyl, an aryl, a cycloheteroalkyl or a heteroaryl having 3 to 6 members, "p"

and "q" being an integer independently selected from 1 to 3, and "p"+"q" being from 2 to 4.

13. The method of claim 1, wherein
$R_1$ is selected from the group consisting of a methyl, —$(CH_2)_a$—C≡CH and —$(CH_2)_b$—$P^+Ph_3$, with "a" being an integer selected from 2 to 4, and "b" being an integer selected from 6 to 10; and
$R_2$ is selected from the group consisting of
—$(CH_2)_d$—C≡CH, with "d" being an integer selected from 2 to 4; and
—$(CH_2)_e$—CH=$CH_2$ with "e" being an integer selected from 2 to 6.

14. The method of claim 1, wherein
$R_1$ is selected from the group consisting of H, a methyl, —$(CH_2)_a$—C≡CH and —$(CH_2)_b$—$P^+Ph_3$, with "a" being an integer selected from 2 to 4, and "b" being an integer selected from 6 to 10;
$R_2$ is selected from the group consisting of
—$(CH_2)_f$—$CR_4$=CH—CH=$CR_5$—$(CH_2)_g$—$R_3$ with $R_4$ and $R_5$ being H, "f" and "g" being an integer independently selected from 1 to 3, and "f"+"g" being from 2 to 4;
—$(CH_2)_f$—C≡C—C≡C—$(CH_2)_g$—$R_3$, with "f" and "g" being an integer independently selected from 1 to 3 and "f"+"g" being from 2 to 4;
—$(CH_2)_i$—$R_3$, with "i" being an integer selected from 7 to 9;
—$(CH_2)_j$—CH[$(CH_2)_k$—$P^+Ph_3$]—$(CH_2)_l$—$R_3$ with "j" and "l" being integer independently selected from 1 to 6, "j"+"l" being from 5 to 7, and "k" being an integer selected from 1 to 6;
—$(CH_2)_m$-cyclobutanyl-$(CH_2)_n$—$R_3$ with "m" and "n" being an integer independently selected from 1 to 3 and "m+n" being from 2 to 4; and
—$(CH_2)_p$—$CHR_6$—CH=CH—$CHR_7$—$(CH_2)_q$—$R_3$ with $R_6$ and $R_7$ being H or forming together a 4-member ring, "p" and "q" being an integer independently selected from 1 to 3 and "p"+"q" being from 2 to 4; and
$R_3$ is

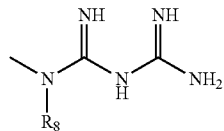

with $R_8$ selected from the group consisting of H, a methyl, $(CH_2)_a$—C≡CH and —$(CH_2)_b$—$P^+Ph_3$, with "a" being an integer selected from 1 to 6 and "b" being an integer selected from 5 to 11.

15. The method of claim 1, wherein at least one among $R_1$, $R_2$ and $R_8$ is —$(CH_2)_a$—C≡CH with "a" being an integer from 1 to 6.

16. The method of claim 1, wherein the compound is selected from the group consisting of

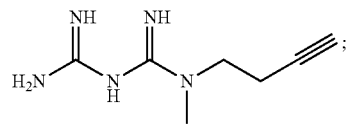

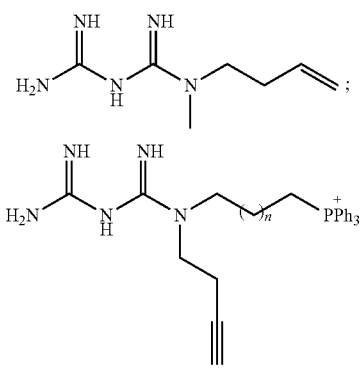

with n being an integer selected from 3 to 9;

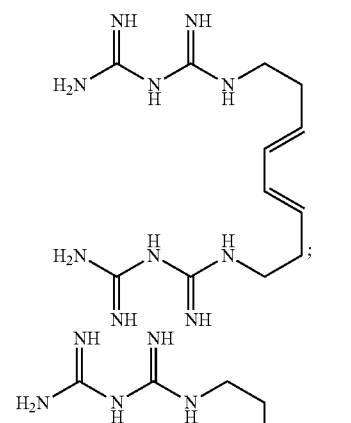

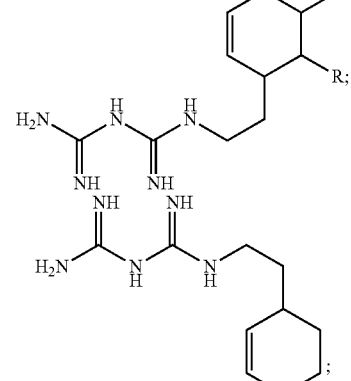

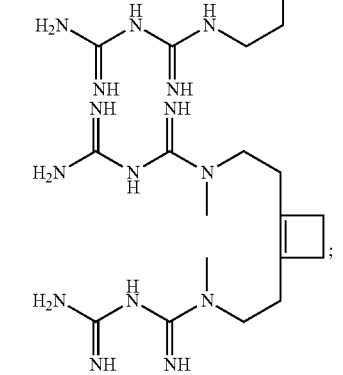

-continued

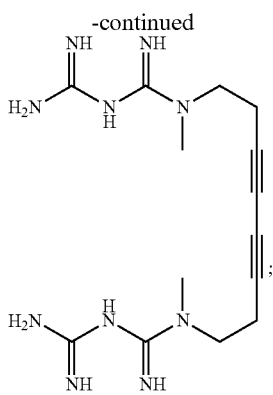

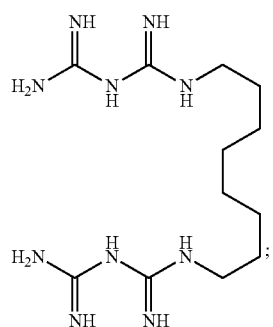

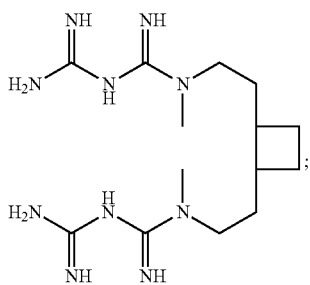

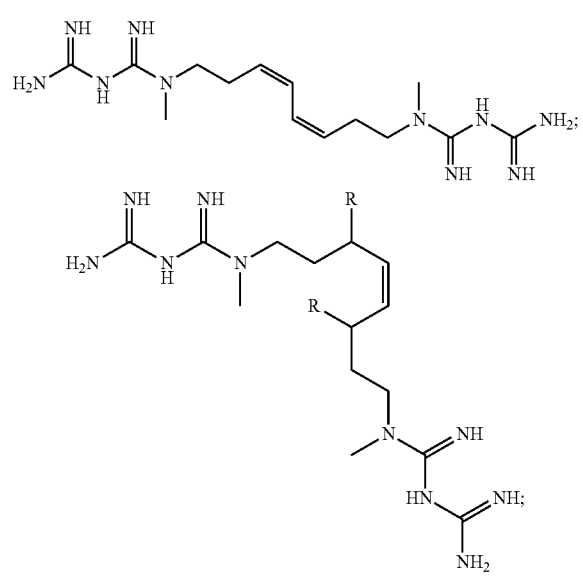

-continued

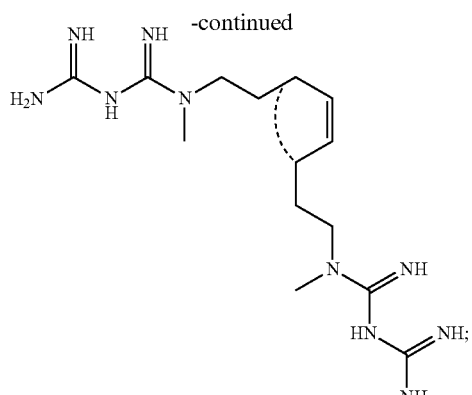

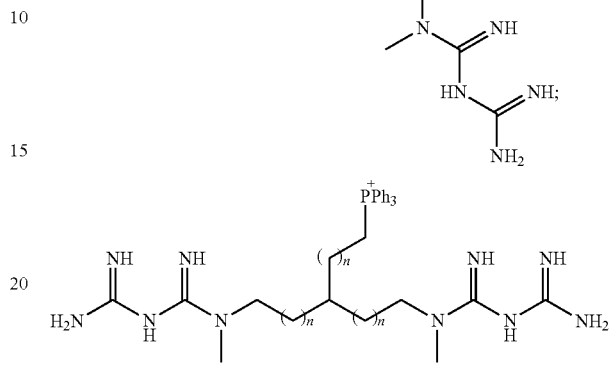

with n being independently an integer selected from 0 to 5;

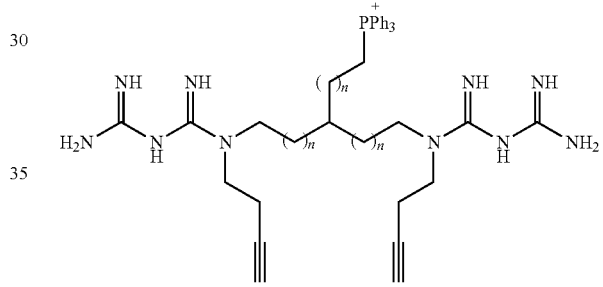

with n being independently an integer selected from 0 to 5; wherein the dotted line being present or absent and being one or two atoms with covalent bonds; and R is selected from the group consisting of a $C_1$-$C_6$ alkyl, a $C_1$-$C_6$ alkyloxy, a $C_1$-$C_6$ halogenoalkyl, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, the group being optionally substituted by a group R'; R' being selected from the group consisting of a $C_1$-$C_6$ alkyl, a $C_1$-$C_6$ alkyloxy, a $C_1$-$C_6$ thioalkyl, a halogen, a $C_1$-$C_6$ halogenoalkyl, a hydroxyl (—OH), a cyano (—CN), a nitro, an amino (—$NH_2$), a carboxyl (—COOH), a phosphate ($PO_4$), an amide (—$CONH_2$), —COOR", —NHR", —NR"R"', —COR", —CONHR", —NHCOR", —$NHSO_2$R", —SOR", —$SO_2$R", —SONR"R"', —$SO_2$NR"R"', a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, said cycloalkyl, cycloheteroalkyl, aryl or heteroaryl being optionally substituted by a halogen, a hydroxyl, a cyano, a nitro, an amino, or a $C_1$-$C_3$ alkoxy, with R" and R"' being H or a $C_1$-$C_6$ alkyl;

or a pharmaceutically acceptable salt thereof.

17. The method of claim 1, wherein the compound is selected from the group consisting of

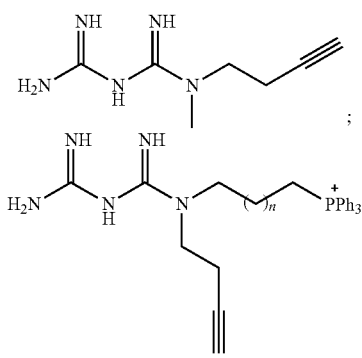

with n being an integer selected from 3 to 9; and

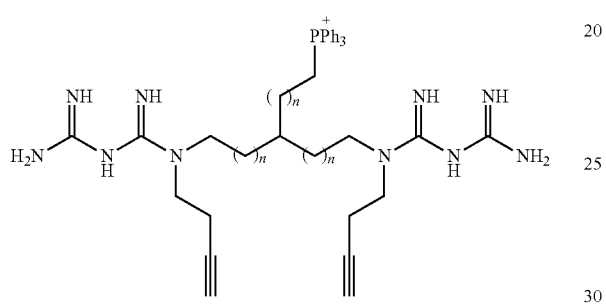

with n being an integer independently selected from 0 to 5, or a pharmaceutically acceptable salt thereof.

18. A method for treating cancer, comprising the administration, to a subject in need thereof, of a compound of formula (I), a conjugate thereof or a pharmaceutical composition comprising said compound or conjugate, said conjugate comprising a drug or a toxin conjugated to an alkyne group in said compound via an azide ($N_3$) group, wherein compound of formula (I) is:

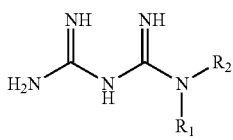

Formula (I)

wherein $R_1$ is selected from the group consisting of a $C_1$-$C_6$ alkyl, —(CH$_2$)$_a$—C≡CH, —(CH$_2$)$_b$—P$^+$Ph$_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6 and "b" being an integer selected from 5 to 11 said alkyl, cycloalkyl, cycloheteroalkyl, aryl or heteroaryl being optionally substituted by a R group or a R' group; and $R_2$ is selected from the group consisting of
—(CH$_2$)$_d$—C≡CH, with "d" being an integer selected from 1 to 6; and
—(CH$_2$)$_e$—CH=CH$_2$ with "e" being an integer selected from 2 to 6;

or $R_1$ is selected from the group consisting of H, a $C_1$-$C_6$ alkyl, —(CH$_2$)$_a$—C≡CH, —(CH$_2$)$_b$—P$^+$Ph$_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6 and "b" being an integer selected from 5 to 11, said alkyl, cycloalkyl, cycloheteroalkyl, aryl or heteroaryl being optionally substituted by a R group or a R' group;

$R_2$ is selected from the group consisting of
—(CH$_2$)$_f$—CR$_4$=CH—CH=CR$_5$—(CH$_2$)$_g$—R$_3$ with $R_4$ and $R_5$ being H, a R group or forming together a six-member ring, optionally substituted by one or two R' groups or fused with a cycloalkyl, an aryl, a cycloheteroalkyl or a heteroaryl having 3 to 6 members, "f" and "g" being an integer independently selected from 1 to 3;
—(CH$_2$)$_f$—C≡C—C≡C—(CH$_2$)$_g$—R$_3$, with "f" and "g" being an integer independently selected from 1 to 3;
—(CH$_2$)$_i$—R$_3$, with "i" being an integer selected from 7 to 9;
—(CH$_2$)$_j$—CH[(CH$_2$)$_k$—P$^+$Ph$_3$]—(CH$_2$)$_l$—R$_3$ with "j" and "l" being integer independently selected from 1 to 6, and "k" being an integer selected from 1 to 6;
—(CH$_2$)$_m$-cyclobutanyl-(CH$_2$)$_n$—R$_3$ with "m" and "n" being an integer independently selected from 1 to 3; and
—(CH$_2$)$_p$—CHR$_6$—CH=CH—CHR$_7$—(CH$_2$)$_q$—R$_3$ with $R_6$ and $R_7$ being H, a R group or forming together a 4-6 member ring, optionally substituted by one or two R' groups or fused with a cycloalkyl, an aryl, a cycloheteroalkyl or a heteroaryl having 3 to 6 members, "p" and "q" being an integer independently selected from 1 to 3; and $R_3$ is

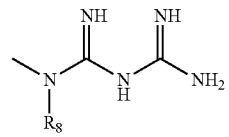

with $R_8$ selected from the group consisting of H, a $C_1$-$C_6$ alkyl, —(CH$_2$)$_a$—C≡CH, —(CH$_2$)$_b$—P$^+$Ph$_3$, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, with "a" being an integer selected from 1 to 6 and "b" being an integer selected from 5 to 11 said alkyl, cycloalkyl, cycloheteroalkyl, aryl or heteroaryl being optionally substituted by a R group or a R' group;

wherein

R is selected from the group consisting of a $C_1$-$C_6$ alkyl, a $C_1$-$C_6$ alkyloxy, a $C_1$-$C_6$ halogenoalkyl, a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, the group being optionally substituted by a group R', R' is selected from the group consisting of a $C_1$-$C_6$ alkyl, a $C_1$-$C_6$ alkyloxy, a $C_1$-$C_6$ thioalkyl, a halogen, a $C_1$-$C_6$ halogenoalkyl, a hydroxyl (—OH), a cyano (—CN), a nitro, an amino (—NH$_2$), a carboxyl (—COOH), a phosphate (PO$_4$), an amide (—CONH$_2$), —COOR", —NHR", —NR"R'", —COR", —CONHR", —NH-COR", —NHSO$_2$R", —SOR", —SO$_2$R", —SONR"R'", —SO$_2$NR"R'", a $C_3$-$C_{10}$ cycloalkyl, a $C_3$-$C_{10}$ cycloheteroalkyl, a $C_6$-$C_{12}$ aryl, and a $C_5$-$C_{12}$ heteroaryl, said cycloalkyl, cycloheteroalkyl, aryl or heteroaryl being optionally substituted by a halogen, a hydroxyl, a cyano, a nitro, an amino, or a $C_1$-$C_3$ alkoxy,
with R" and R''' being H or a $C_1$-$C_6$ alkyl;
or a pharmaceutically acceptable salt thereof.

19. The method of claim 18, wherein the cancer is a cancer with mesenchymal cells.

20. The method of claim 18, wherein the cancer is selected from the group consisting of rectal cancer, colorectal cancer, stomach cancer, head and neck cancer, thyroid cancer, cervical cancer, uterine cancer, breast cancer, triple negative breast cancer, ovarian cancer, brain cancer, glioblastoma, neuroblastoma, lung cancer, small-cell lung cancer, non-small-cell lung cancer, skin cancer, bladder cancer, blood cancer, renal cancer, liver cancer, prostate cancer, multiple myeloma, and endometrial cancer.

21. The method of claim 18, further comprising treatment comprising radiotherapy chemotherapy, hormonotherapy or immunotherapy.

22. The method of claim 4, wherein the subject has breast cancer.

23. The method of claim 8, wherein the cancer with mesenchymal cells is breast cancer.

24. The method of claim 19, wherein the cancer with mesenchymal cells is breast cancer.

\* \* \* \* \*